United States Patent
Tsugita et al.

(10) Patent No.: US 6,176,851 B1
(45) Date of Patent: *Jan. 23, 2001

(54) CARDIOPLEGIA OCCLUDER

(75) Inventors: Ross S. Tsugita, Mountain View; Tracy D. Maahs, Santa Clara, both of CA (US)

(73) Assignee: Embol-X, Inc., Mountain View, CA (US)

( * ) Notice: Under 35 U.S.C. 154(b), the term of this patent shall be extended for 0 days.

This patent is subject to a terminal disclaimer.

(21) Appl. No.: 09/387,634

(22) Filed: Aug. 31, 1999

Related U.S. Application Data

(63) Continuation of application No. 08/993,202, filed on Dec. 18, 1997, now Pat. No. 6,048,331, which is a continuation-in-part of application No. 08/854,806, filed on May 12, 1997, which is a continuation-in-part of application No. 08/645,762, filed on May 14, 1996, now abandoned.

(51) Int. Cl.[7] ................................................. A61M 29/00
(52) U.S. Cl. ............................................. 604/509; 604/96
(58) Field of Search ........................... 604/96, 101, 100, 604/912, 915, 920, 921, 28, 500, 508–510; 606/191–194; 600/16–18

(56) References Cited

U.S. PATENT DOCUMENTS

| | | | |
|---|---|---|---|
| 4,119,100 | * | 10/1978 | Rickett ................................. 604/96 |
| 4,771,776 | * | 9/1988 | Powell et al. ........................ 604/96 |
| 5,036,868 | * | 8/1991 | Berggren et al. ..................... 604/96 |
| 5,122,115 | * | 6/1992 | Marks .................................. 604/96 |
| 5,273,534 | * | 12/1993 | Knoepfler ............................. 604/96 |
| 5,308,325 | * | 5/1994 | Quinn et al. ......................... 604/96 |
| 5,312,344 | * | 5/1994 | Grinfeld et al. ..................... 604/96 |
| 5,425,708 | * | 6/1995 | Nasu ................................... 604/96 |
| 5,505,698 | * | 4/1996 | Booth et al. ......................... 604/96 |
| 5,571,161 | * | 11/1996 | Starksen ............................. 604/96 |
| 5,800,375 | * | 9/1998 | Sweezer et al. .................... 604/96 |
| 5,807,326 | * | 9/1998 | O'Neill et al. ...................... 604/96 |
| 5,820,593 | * | 10/1998 | Sofar et al. ......................... 604/96 |
| 5,928,192 | * | 7/1999 | Maahs ................................. 604/96 |

FOREIGN PATENT DOCUMENTS

| | | | |
|---|---|---|---|
| 0218275 | * | 4/1987 | (EP) . |
| 764684 | | 9/1980 | (SU) . |

\* cited by examiner

*Primary Examiner*—Wynn Wood Coggins
*Assistant Examiner*—Manuel Mendez
(74) *Attorney, Agent, or Firm*—Lyon & Lyon LLP

(57) ABSTRACT

A cardioplegia occluder and methods of using the device during cardiac surgery are disclosed. The system typically includes a substantially rigid cannula with an occluder mounted on the distal region of the cannula that expands upon activation to occlude the aorta downstream of an infusion port which delivers cardioplegia solution to arrest the heart. Systems including cutting blades, blade guards, flanges, radiopaque markers and occluder aligners are also disclosed. In use, the distal end of the cannula is inserted through an incision into the aorta, the occluder is expanded and cardioplegia solution is infused upstream of the aorta to arrest the heart. The infusion port can alternately be used to aspirate cardioplegia or embolic debris or other unwanted material from the aorta.

20 Claims, 20 Drawing Sheets

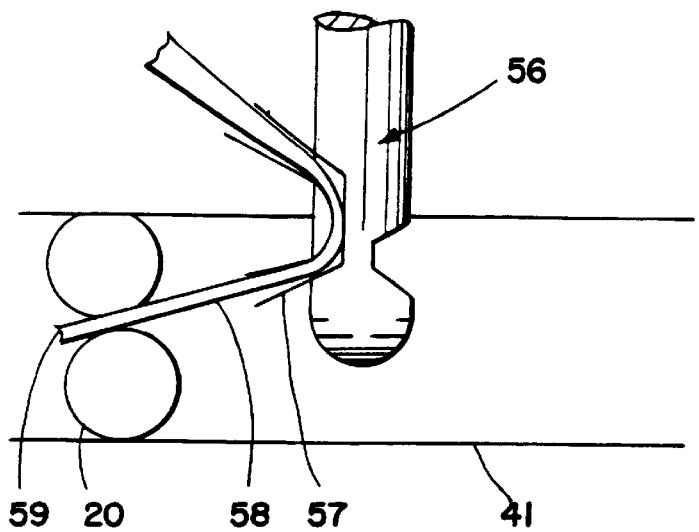
Fig. 5
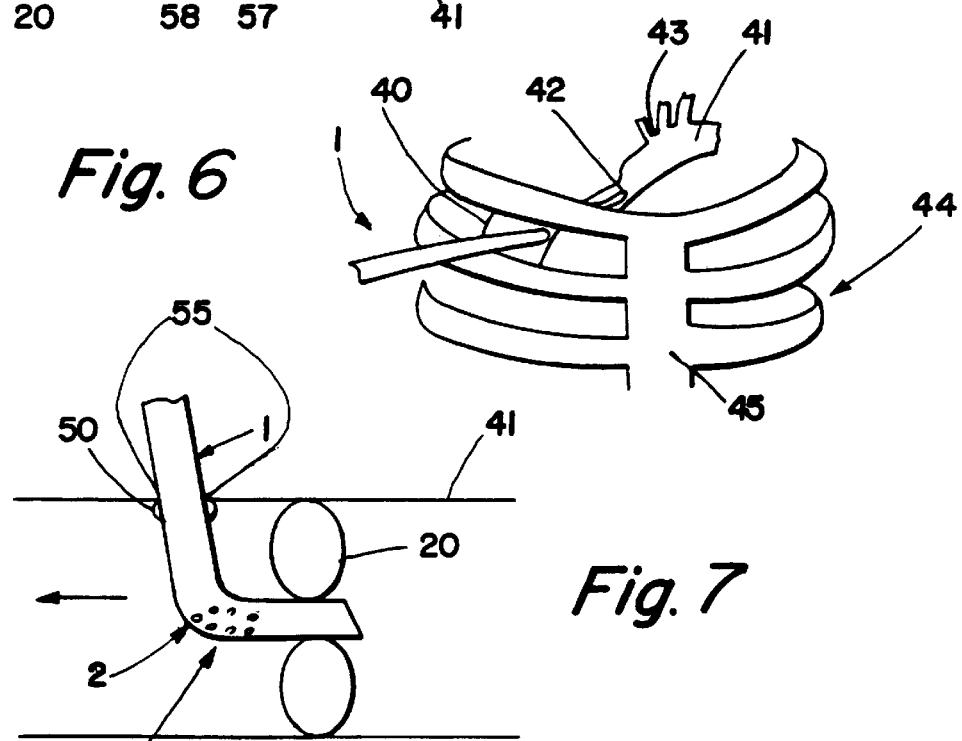
Fig. 6
Fig. 7
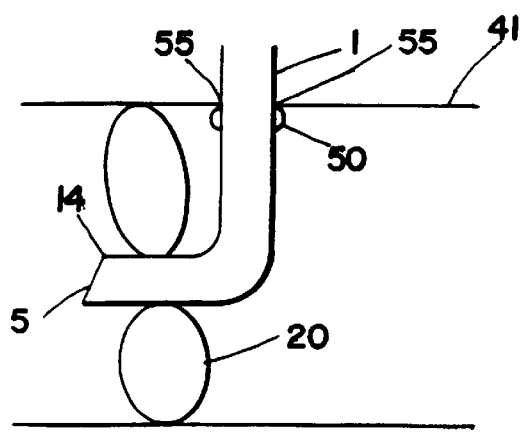
Fig. 7A

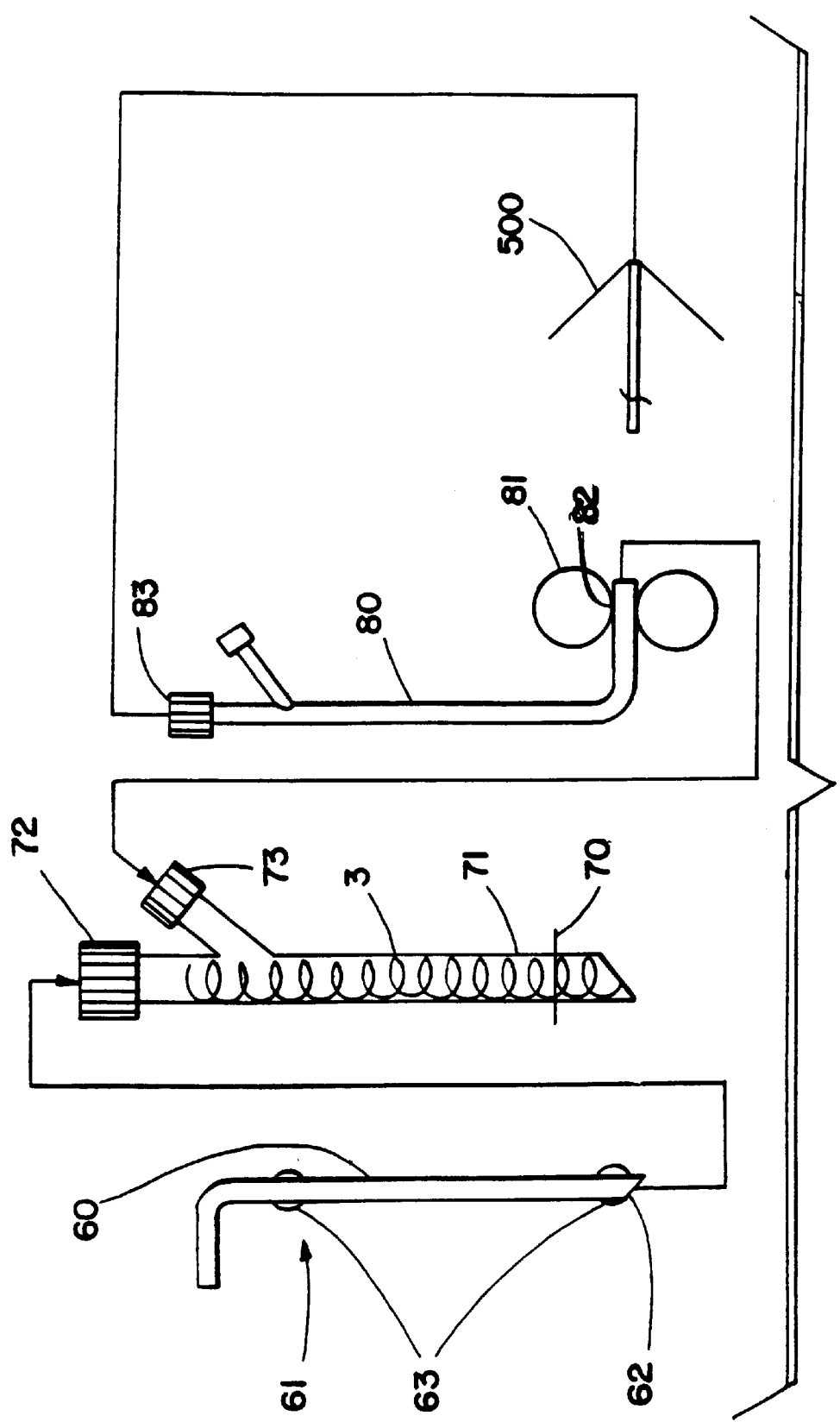

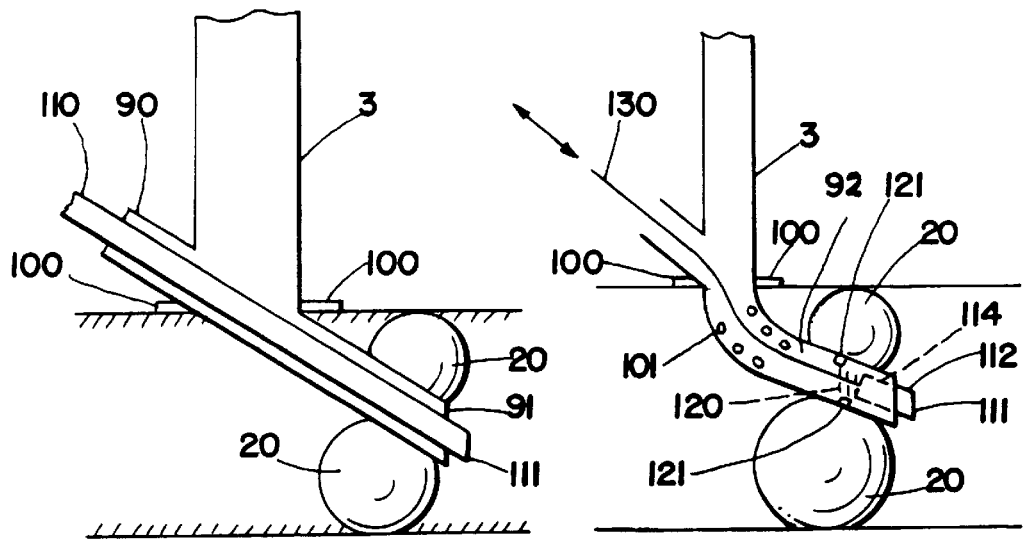
Fig. 9          Fig. 10
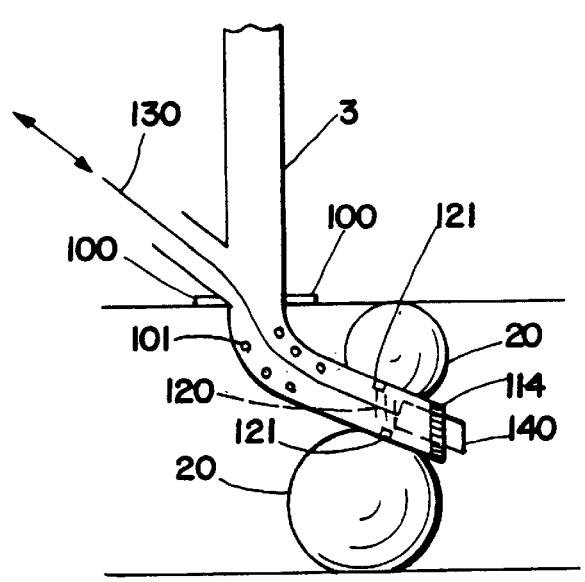    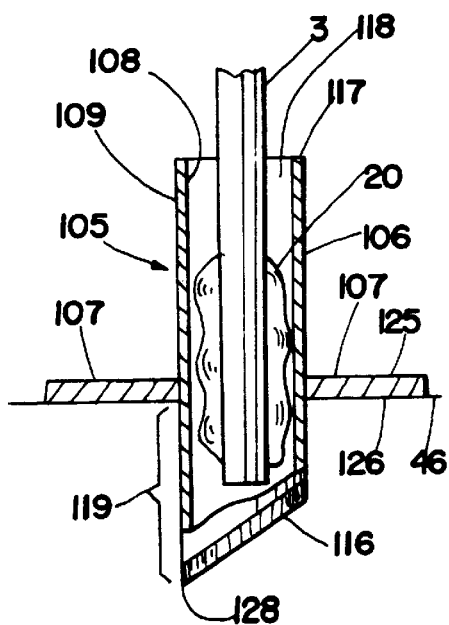
Fig. 10A        Fig. 11

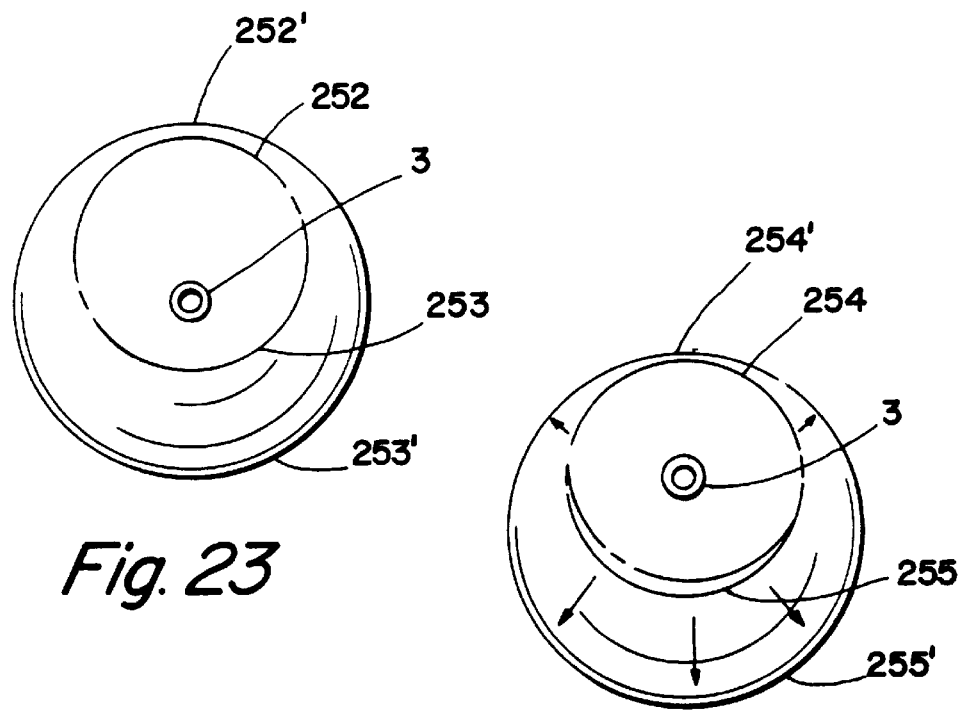
Fig. 23
Fig. 24
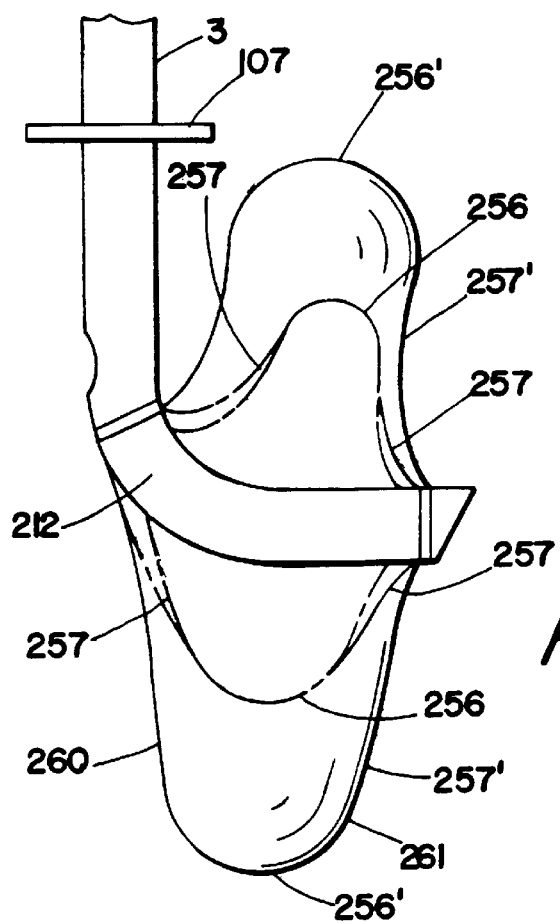
Fig. 25

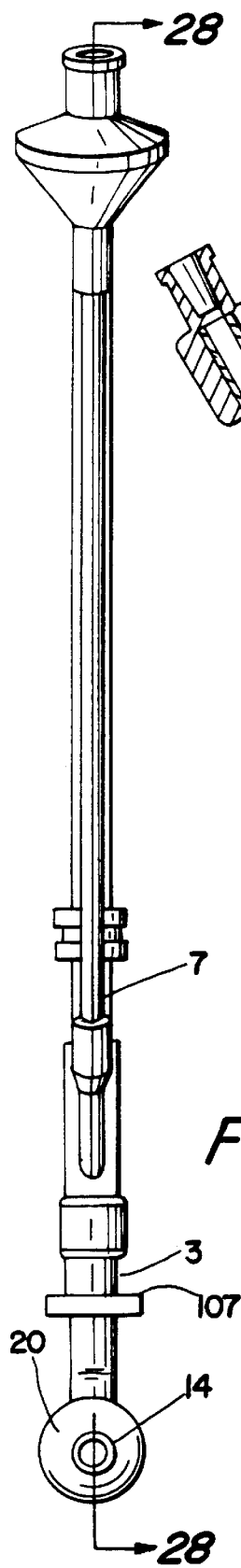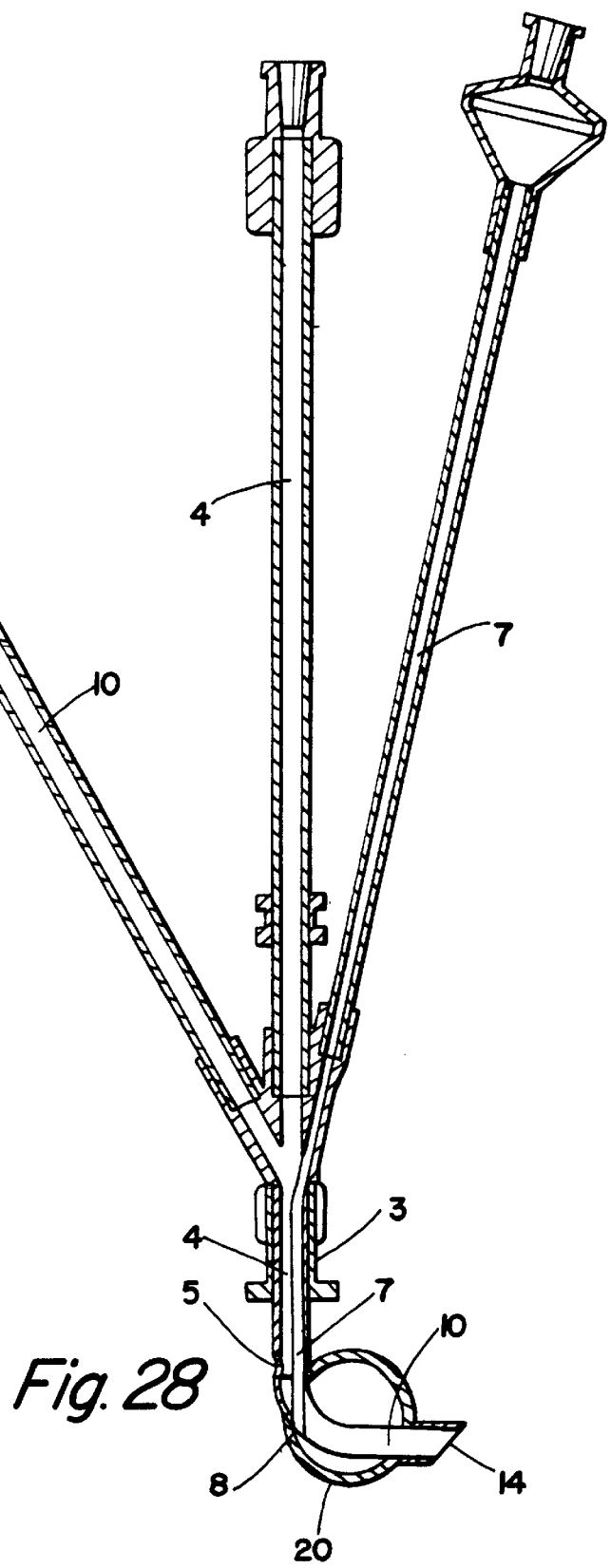

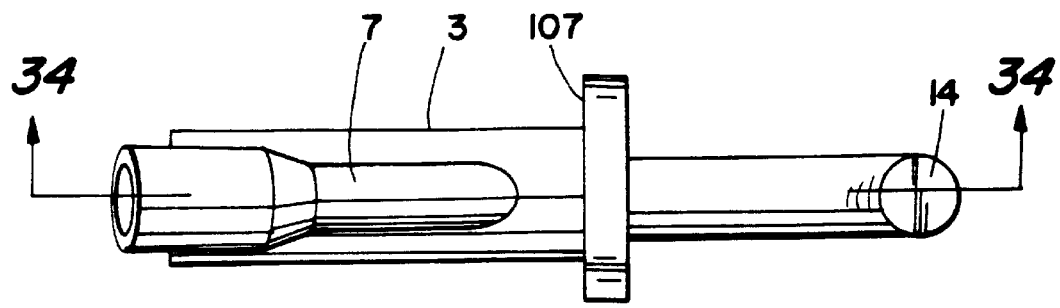
Fig. 29
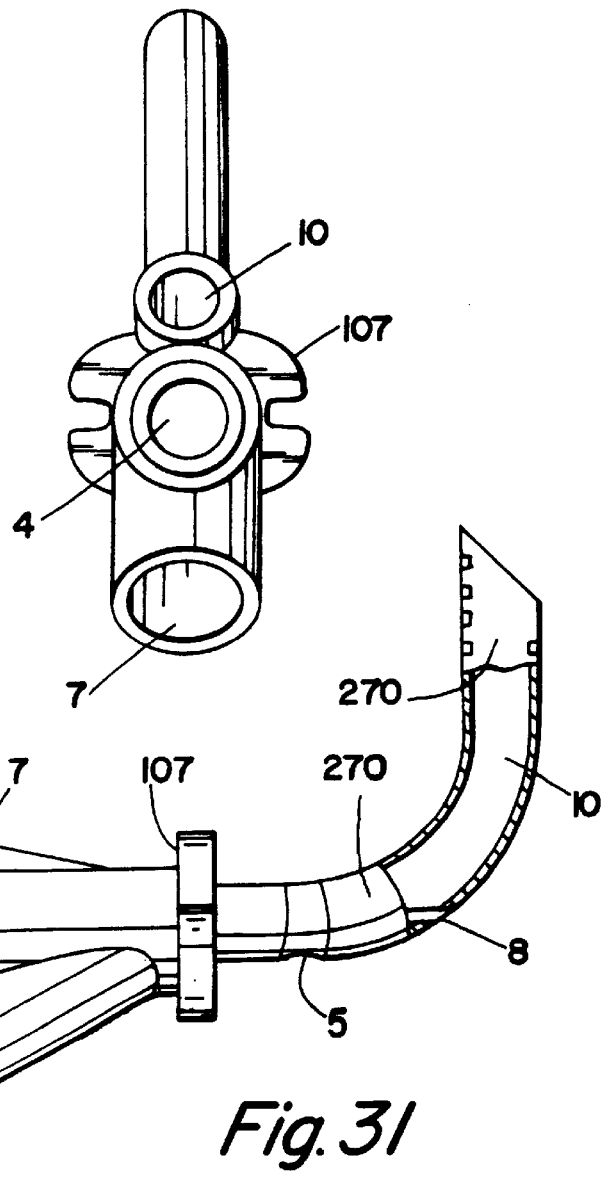
Fig. 30
Fig. 31

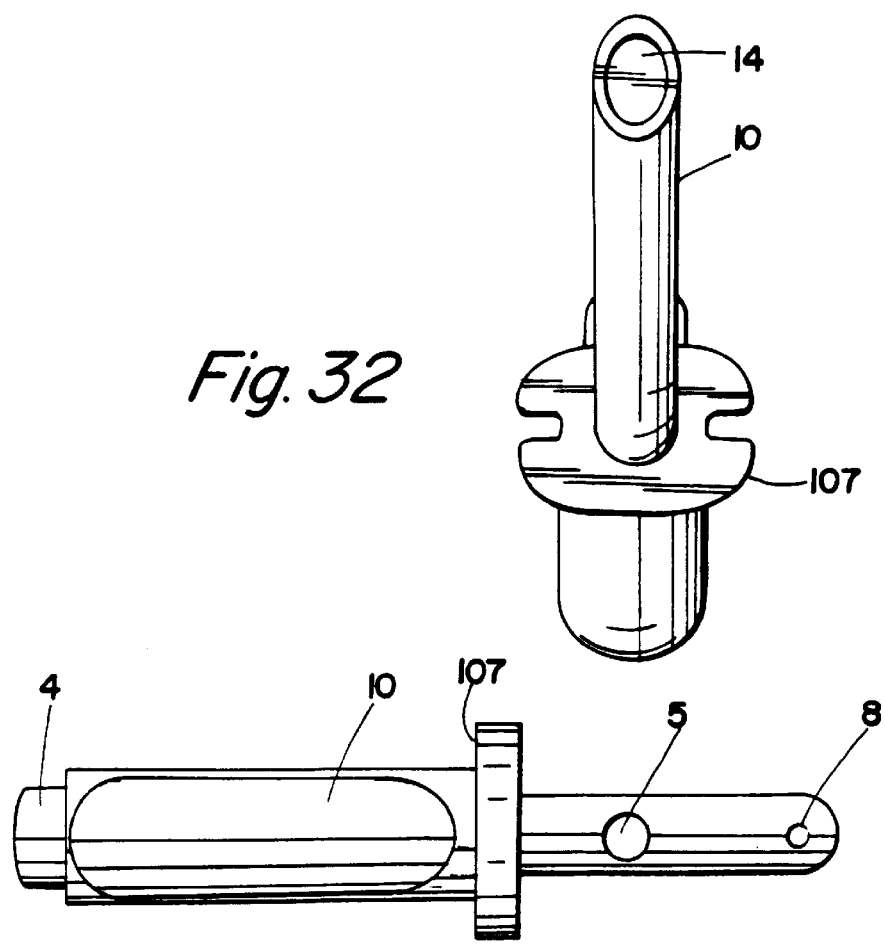
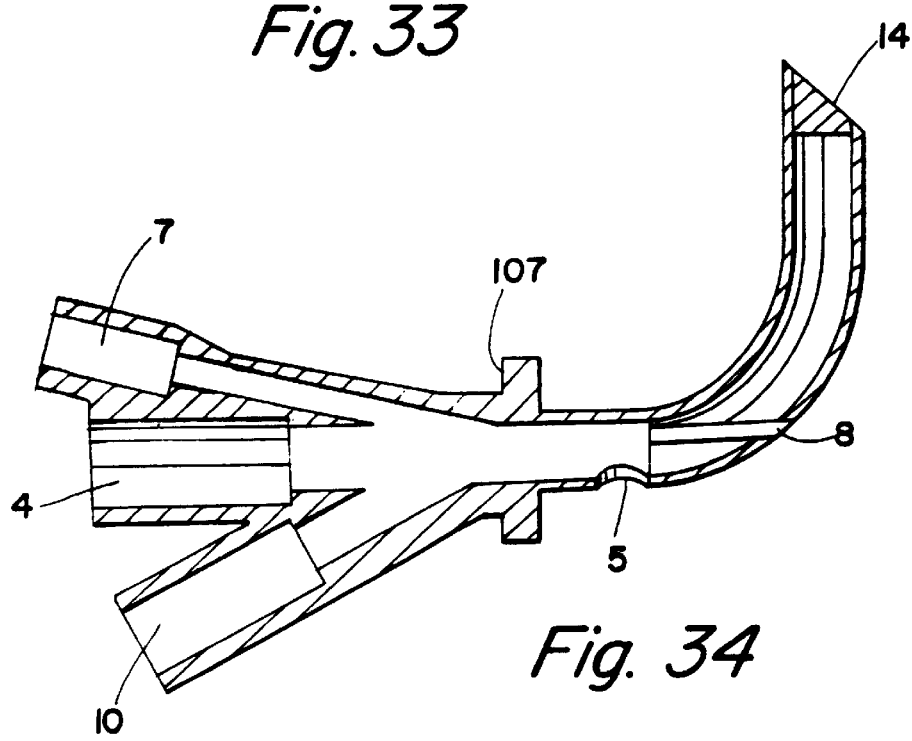

CARDIOPLEGIA OCCLUDER

This is a continuation of U.S. application Ser. No. 08/993,202, filed Dec. 18, 1997, now U.S. Pat. No. 6,048,331, which is a continuation-in-part of U.S. application Ser. No. 08/854,806, filed May 12, 1997, which is a continuation-in-part of U.S. application Ser. No. 08/645,762, filed May 14, 1996, now abandoned. The contents of these prior applications are expressly incorporated herein by reference in their entirety.

FIELD OF THE INVENTION

This invention relates to methods and apparatus for administering cardioplegia to the aorta during cardiac surgery. The devices include a cardioplegia occluder that can include various features such as a cutting blade, a blade guard, a flange, radiopaque markers and an occluder aligner to properly position the distal end of the device within the aorta. Once the cardioplegia occluder is in its proper position, the occluder is expanded to occlude the aorta downstream of the infusion port and cardioplegia solution is then introduced through the infusion port to arrest the heart. The infusion port can alternately be used to aspirate cardioplegia or embolic debris or other unwanted material from the aorta.

BACKGROUND

Currently, the most common method of temporarily occluding the ascending aorta and arresting the heart during open heart surgery utilizes a mechanical cross clamp and a cardioplegia cannula. Once the chest cavity has been opened, access to the heart and to the adjacent vessels is provided. The ascending aorta is partially dissected from the surrounding tissue and exposed. Arterial and venous cannulas are inserted and sutured into place. The cannulas are connected to the cardiopulmonary bypass machine, and bypass blood oxygenation is established.

At this point, the heart must be arrested and isolated from the rest of the circulatory system. A mechanical cross clamp is positioned between the cardioplegia cannula and the aortic cannula and is actuated. The aorta is completely collapsed at the clamp site, thus stopping flow of blood between the coronary arteries and the innominate artery, and the oxygenated bypass blood is shunted around the heart. Once the vessel occlusion has been completed, cardioplegia solution is introduced through the cardioplegia cannula to arrest the heart. The surgeon may now proceed with the desired operation.

Other less common means of occluding the aorta include percutaneous balloon catheter occlusion, direct aortic balloon catheter (Foley) occlusion, aortic balloon catheter occlusion, and an inflating diaphragm occluder (Hill—occlusion trocar). The percutaneous balloon catheter is inserted typically from the femoral artery feed through the descending aorta, across the aortic arch into position in the ascending aorta. Once in the ascending aorta, the balloon occluder is inflated and flow stopped.

As a simple replacement for the mechanical cross clamp, a Foley catheter may be placed through an additional incision site near the standard cross clamp site. Once inserted, the Foley catheter balloon is inflated and flow is stopped. Similarly, an aortic balloon catheter is placed directly into the aorta. This catheter replaces the standard aortic cannula by delivering the CPB blood back to the arterial circulatory system. The occluder balloon is located on the catheter proximal to CPB blood exit port on the cannula. The occlusion trocar is desired to offer similar features as the aortic balloon occluder cannula and would be used in place of the standard aortic cannula. However, it relies on an inflatable diaphragm to occlude the vessel.

The use of a balloon to occlude an artery has been disclosed by Gabbay, U.S. Pat. No. 5,330,451 (this and all other references cited herein are expressly incorporated by reference as if fully set forth in their entirety herein). The Gabbay device included a perfusion cannula having a proximal balloon occluder and a distal intra-aortic balloon to divert blood to the carotid arteries. The Gabbay perfusion cannula is disclosed for use during open heart surgery in order to prevent complications associated therewith.

Moreover, Peters, U.S. Pat. No. 5,433,700, discusses a method for inducing cardioplegic arrest using an arterial balloon catheter to occlude the ascending aorta. The Peters method includes the steps of maintaining systemic circulation using peripheral cardiopulmonary bypass, venting the left side of the heart, and introducing a cardioplegic agent into the coronary circulation. This procedure is said to prepare the heart for a variety of surgical procedures. Disclosures of similar endovascular occlusion catheters can be found in Machold et al., U.S. Pat. No. 5,458,574, Stevens, International Application No. PCT/US93/12323, Stevens et al., International Application No. PCT/US94/12986, Nasu, U.S. Pat. No. 5,425,708 and Grinfeld et al., U.S. Pat. No. 5,312,344.

Each of the existing methods of blocking aortic blood flow and arresting the heart carries with it some undesired aspects. The mechanical cross clamp offers simplicity and reliably consistent operation. However, the physical clamping action on the vessel has been linked to many adverse body responses. Barbut et al. ("Cerebral Emboli Detected During Bypass Surgery Are Associated With Clamp Removal," *Stroke*, 25(12):2398–2402 (1994), incorporated herein by reference in its entirety) noted the majority of embolic events (release) is associated with the actuation and release of the cross clamp during coronary bypass graph surgery. The clamping action may be responsible for breaking up and freeing atherosclerotic buildup on the vessel walls. In addition, the potential for vascular damage, like aortic dissections, may also incur during the clamp application.

The percutaneous balloon catheter occluder has a distinct drawback in that it must be placed with visionary assistance. Fluoroscopy is typically used to position the device in the aorta. This added equipment is not always readily available in the surgical suite. In addition, the catheter placement up to the aorta may also create additional vascular trauma and emboli generation.

The use of a Foley catheter to occlude the aorta requires an additional incision site to place the device. The extra cut is an additional insult site and requires sutures to close. Generation of emboli and the potential of aortic dissection directly associated with just the incision may potentially outweigh the benefits of using the catheter.

The aortic balloon occluder cannula addresses many of the deficiencies of the previous devices. Placement is easy to visualize, no extra cuts are required, and there is no need for the potentially traumatic cross clamp. However the currently-available aortic balloon occluders suffer from problems of migration within the ascending aorta because the cannulas on which the balloons are mounted are typically flexible tubes as disclosed by Grinfeld et al. and Nasu. Attempts to solve the migration problem include balloon designs with a large "footprint" in the distal region of the cannula. (See Nasu, supra.) This large footprint balloon is a less than adequate solution because it encroaches into the already limited area of the ascending aorta in which surgical access is available. Further, use of each of these aortic occluding balloons requires a cardioplegia cannula to be inserted through an additional incision site to arrest the heart.

A need exists for an aortic cannula having both a balloon occluder which can isolate the ascending aorta from peripheral vasculature without substantial migration of the occluder into the ascending aorta, thereby reducing or eliminating the need for aortic cross-clamping, and an associated cardioplegia infusion port which eliminates the need for a separate incision for a cardioplegia cannula. Existing devices are inadequate for this purpose.

SUMMARY OF THE INVENTION

The present invention relates to medical devices and their methods of use, and particularly cardioplegia occluders. The cardioplegia occluders comprise a cannula having an occluder to isolate the ascending aorta from peripheral vasculature during cardiac surgery and an infusion port for administering cardioplegia to arrest the heart. The infusion port can alternately be used to aspirate cardioplegia or embolic debris or other unwanted material from the aorta. The devices of the present invention may include various features such as a cutting blade, a blade guard, a flange, radiopaque markers and an occluder aligner to properly position the distal end of the device within the aorta.

In one embodiment, the device includes a substantially rigid cannula adapted to enter the aorta with a proximal end that receives cardioplegia solution into a cardioplegia lumen and delivers it to an infusion port in the distal region of the cannula. An occluder, mounted on the distal region of the cannula, expands away from the cannula upon activation to substantially occlude the aorta downstream from the infusion port. During use, the occluder isolates the ascending aorta from the peripheral vasculature. The substantially rigid nature of the cannula inhibits migration of the occluder into the ascending aorta, thus overcoming problems associated with other currently available aortic balloon cannulas. In certain embodiments, the occluder is an inflatable balloon. In other embodiments, the occluder is a foam-filled, self-expanding balloon. Certain balloon embodiments also include a lumen which can be used to inflate the balloon or alternately can be used to apply negative pressure to deflate the balloon. Other embodiments include an aspiration lumen which terminates at the infusion port so that the infusion port can alternately be used to deliver cardioplegia solution or aspirate embolic debris and other unwanted material from the aorta. Another embodiment further includes an occluder aligner to help position the distal end of the cannula within the aorta and to stabilize the position of the occluder during expansion.

In another embodiment, the device includes a cannula associated with a cutting blade which is adapted to cut through the wall of the aorta to allow introduction of the cannula. The proximal end of the cannula is adapted to receive cardioplegia solution into a cardioplegia lumen and deliver it to an infusion port in the distal region of the cannula. An occluder mounted on the distal region of the cannula expands away from the cannula upon activation to substantially occlude the aorta downstream from the infusion port. During use, the occluder isolates the ascending aorta from the peripheral vasculature. Certain embodiments also include a blade guard which moves when pressed against the aorta to allow the blade to cut through the wall of the aorta and then repositions to prevent the blade from cutting. Other embodiments further include an occluder aligner, a lumen which can be used to inflate the or deflate the balloon or an aspiration lumen which terminates with the infusion port.

The methods of the present invention include administering cardioplegia to the aorta during cardiac surgery using a cardioplegia occluder as described above. An incision is made in the aorta, and the distal end of the cannula is inserted through the incision. The occluder is expanded to occlude the aorta and thereby isolate the ascending aorta from peripheral circulation without substantial migration of the occluder within the ascending aorta. Cardioplegia solution is then infused through the infusion port to arrest the heart. In embodiments that include a cutting blade, the step of making the incision in the aorta is performed by the cutting blade. In embodiments that include an aspiration lumen, the method further includes the step of aspirating cardioplegia and embolic debris from the aorta by applying negative pressure to the aspiration lumen.

BRIEF DESCRIPTION OF DRAWINGS

Reference is now made to a brief description of the drawings, which are intended to illustrate a cardioplegia occluder for use herein. The drawings and detailed description which follow are intended to be merely illustrative and are not intended to limit the scope of the invention as set forth in the appended claims.

FIG. 5 depicts an embodiment of a cannula with a side channel having a cardioplegia occluder.

FIG. 6 shows the cardioplegia occluder inserted into the aorta via a minimally invasive chest port.

FIG. 7 depicts a lateral cross-section of an embodiment having an L-shaped cannula with infusion ports proximal to the occluder.

FIG. 7A depicts a lateral cross-section of an embodiment having an L-shaped cannula with an infusion port at the distal end of the cannula.

FIG. 8 shows a lateral view of an embodiment with a separately insertable balloon cannula, a separately insertable filter cannula and a separately insertable cutting blade.

FIG. 9 depicts a lateral cross-section of an embodiment with an angled retractable cutting blade.

FIG. 10 depicts a lateral cross-section of an embodiment with a spring-mounted retractable cutting blade and a curved distal region of the cannula which can serve as a blade guard.

FIG. 10A depicts a lateral cross-section of an embodiment where the end of the distal region is sharpened to form a cutting blade and the blade guard is a retractable obturator received through the cutting blade.

FIG. 11 shows a lateral cross-section of an embodiment with a balloon cannula slideably inserted in a flange sleeve where the distal end of the flange sleeve is sharpened to form a cutting blade.

FIG. 23 shows an embodiment of an asymmetric occluder that is a balloon with a thick region and a thin region where the asymmetric configuration of the balloon is shown in a collapsed condition, and when expanded, the balloon becomes symmetric.

FIG. 24 shows an embodiment of an symmetric occluder that is a balloon with a higher shore region and a lower shore region where the symmetric configuration of the balloon is shown in a collapsed condition and, when expanded, the balloon becomes asymmetric.

FIG. 25 depicts an embodiment where the occluder is a balloon with walls of varying thickness.

FIG. 27 is a front view of the embodiment of FIG. 26.

FIG. 28 is a lateral cross-section of the embodiment of FIG. 27 shown through section line 28—28.

FIG. 29 is a front view of the distal region of the cannula of the embodiment of FIG. 26 showing the closed distal end.

FIG. 30 is a top elevation of the embodiment of FIG. 29.

FIG. 31 is a lateral view of the embodiment of FIG. 29 with a partial cross-section.

FIG. 32 is a bottom elevation of the embodiment of FIG. 29 showing the closed distal end.

FIG. 33 is a back elevation of the embodiment of FIG. 29.

FIG. 34 is a lateral cross-section of the embodiment of FIG. 29 shown through section line 34—34.

DETAILED DESCRIPTION

Figure 1:
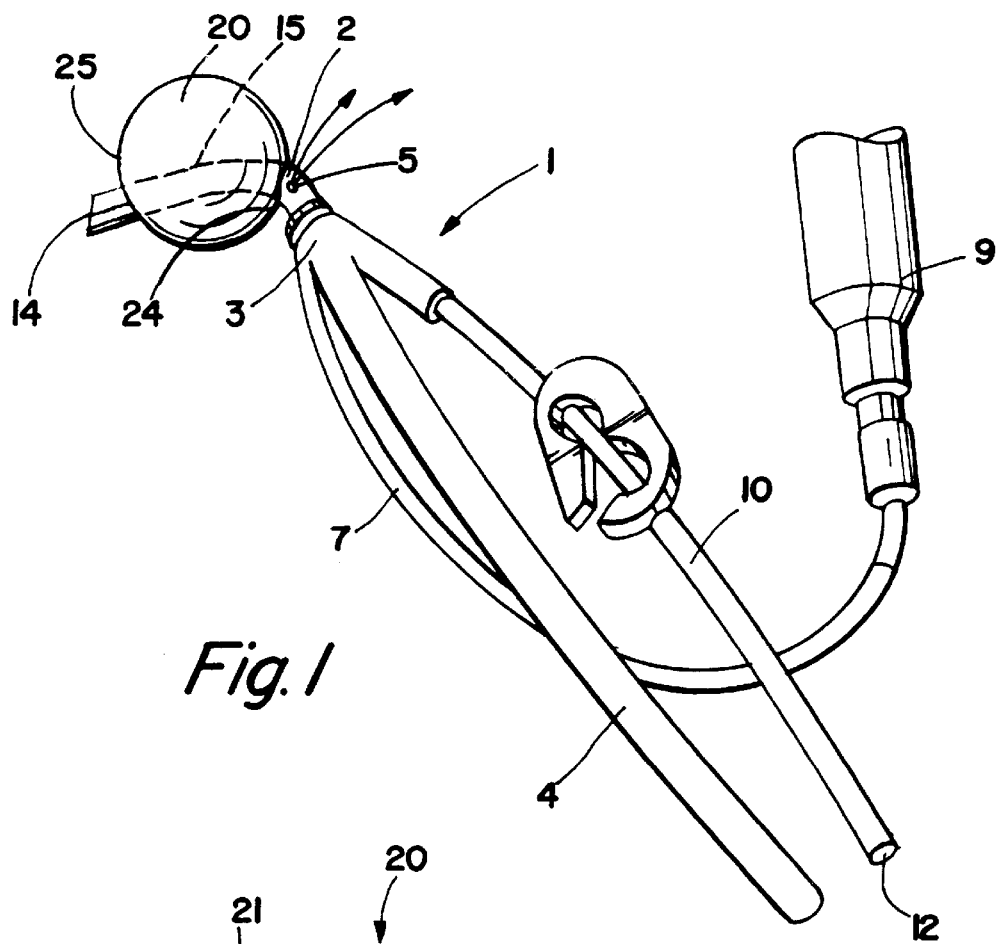
FIG. 1 depicts an embodiment of a cardioplegia occluder with a cannula having three lumens.

FIG. 1 depicts an embodiment of a cardioplegia occluder 1 for delivering cardioplegia to the aorta during cardiopulmonary bypass where the distal region 2 of the substantially rigid cannula 3 is curved to facilitate self-centering inside the aorta. The distal end of the cannula 14 is adapted to enter the aorta.

Figure 2:
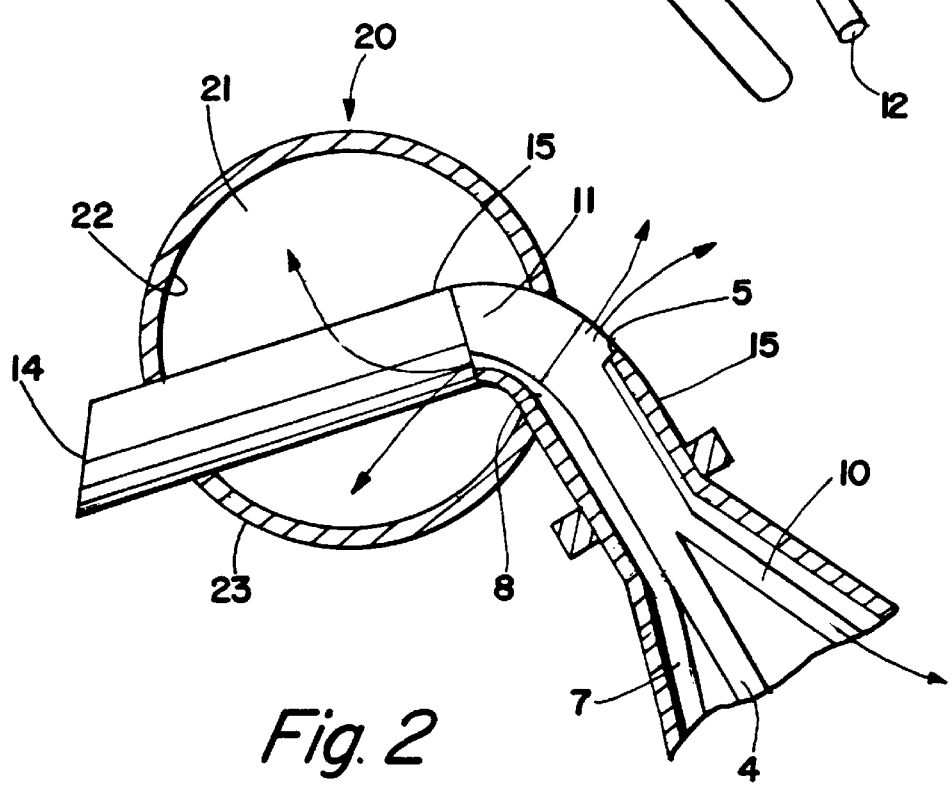
FIG. 2 depicts a lateral cross-section of the distal region of the embodiment of FIG. 1.

In this embodiment, a spherical occluder 20 is circumferentially disposed about the outer surface 15 of the distal region of the cannula forming a chamber 21 with an inner surface 22, an outer surface, a proximal end 24 and a distal end. In some embodiments, the occluder is an inflatable balloon. In other embodiments, the balloon is foam-filled, so that the occluder may be inserted in a contracted condition, for instance, within a sleeve or under negative pressure, and when released from the sleeve or the negative pressure, will automatically expand to the predetermined shape. Although FIG. 1 and FIG. 2 depict the occluder as spherical, in other embodiments, it is conical, elliptical or funnel shaped. In the embodiment of FIG. 1 and FIG. 2, the occluder is an inflatable balloon covering a portion of the curved distal region of the cannula. In certain embodiments, the occluder is circumferentially disposed about the distal region of the cannula so that the cannula runs through the longitudinal center axis of the occluder. In other embodiments, the occluder is circumferentially disposed about the distal region of the cannula so that the cannula runs through a region displaced laterally from the longitudinal center axis of the occluder. For a detailed discussion of the construction of a balloon occluder disposed on a cannula, the reader is referred to copending U.S. Applications Barbut et al., Ser. No. 08/645,762, filed May 14, 1996, and Tsugita et al., Ser. No. 08/854,806, filed May 12, 1997, both expressly incorporated herein by reference.

The cannula is typically a rigid or semi-rigid, preferably transparent tube having a proximal end adapted to receive cardioplegia solution and a cardioplegia lumen which extends distally from the proximal end and terminates and communicates with an infusion port in the distal region for delivery of cardioplegia solution to the aorta. The occluder, which has a longitudinal center axis, is mounted on the distal region of the cannula. The occluder is expandable between a contracted condition and an expanded condition, wherein the occluder, when contracted, is closely associated with the outer surface of the cannula, while the occluder expands upon activation to substantially occlude the aorta downstream of the infusion port. During use, the occluder isolates the ascending aorta from the peripheral vasculature without substantial migration of the occluder into the ascending aorta. Because of the substantially rigid condition of the cannula, the balloon may have a relatively small footprint where it is coupled to the distal region of the cannula without substantial migration of the occluder into the ascending aorta.

The embodiment shown in FIG. 1 and FIG. 2 has three lumens within the cannula. Other embodiments may have more or fewer lumens. In some embodiments, certain lumens are separate, non-communicating channels. In certain embodiments, the lumens are generally substantially cylindrical, semi-rigid and preferably transparent. In FIG. 1 and FIG. 2, a cardioplegia lumen 4 is adapted to receive cardioplegia through its proximal end and deliver it to an infusion port 5 at its distal end. The infusion port 5 is proximal to the occluder, so that when the occluder is in an expanded condition, cardioplegia infuses to a region upstream from the occluded aorta. Another lumen 7 is adapted to receive fluid through its proximal end and deliver it to an inflation port 8 at the distal end of the lumen where it terminates and is in fluid communication with the chamber 21 of the occluder. When the occluder is contracted, it is closely associated with the cannula's outer surface 15. When fluid is delivered to the chamber of the occluder through the inflation port, the occluder expands away from the cannula, as depicted in FIG. 1 and FIG. 2. In one embodiment, the pressurized fluid used to fill the chamber of the occluder is saline solution and in another embodiment, it is gas. In another embodiment, negative pressure may be applied to the lumen 7 to contract a foam-filled balloon. An aspiration lumen 10 has a proximal end 12 adapted to couple to an aspirator, and extends distally from the proximal end and terminates and communicates with the infusion port 5. In embodiments having an aspiration lumen, the infusion port can alternately deliver cardioplegia solution or aspirate embolic debris and other unwanted material from the aorta.

Figure 3:
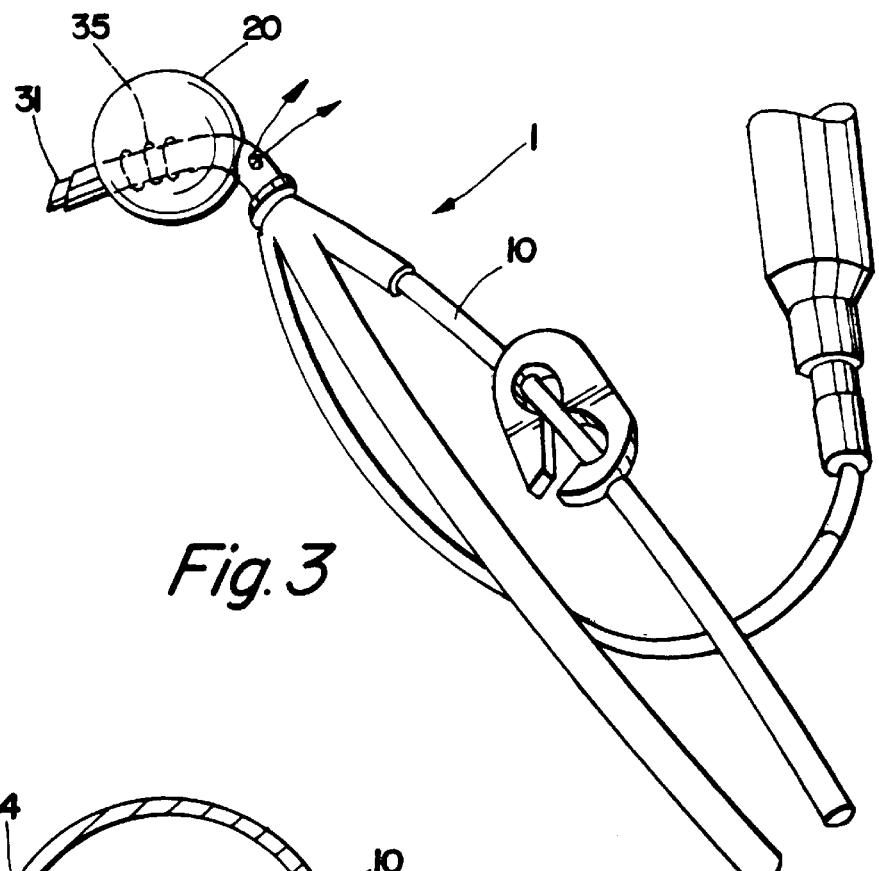
FIG. 3 depicts another embodiment of a cardioplegia occluder with a cutting blade and a retractable blade guard.
Figure 4:
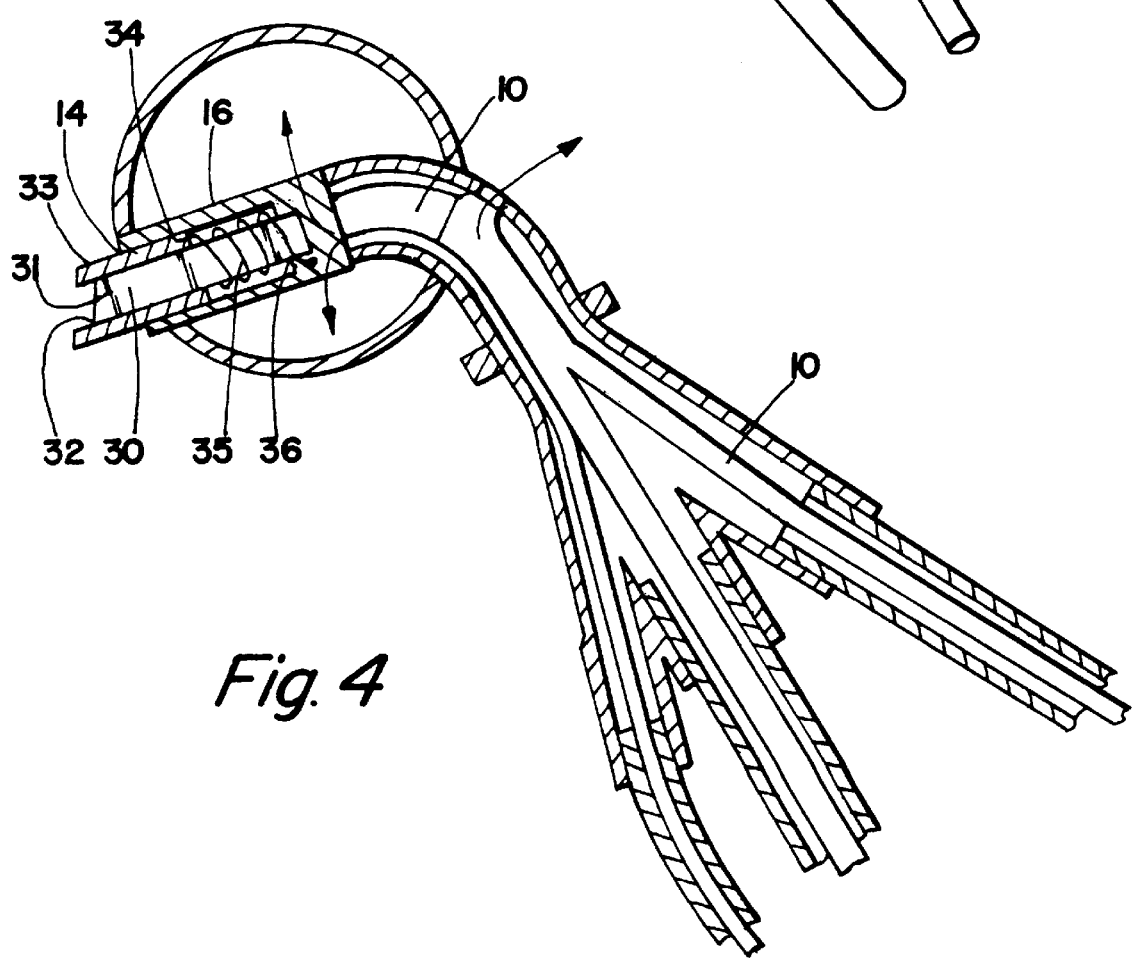
FIG. 4 depicts a lateral cross-section of the distal region of the embodiment of FIG. 3.

FIG. 3 and FIG. 4 depict another embodiment of the cardioplegia occluder 1 where the distal end 16 of the cannula 10 is open forming a cutting blade lumen to receive the cutting blade 30. The distal end 31 of the cutting blade, which when exposed, protrudes beyond the in the distal end of the cannula, has a sharpened tip 32 adapted to cut through the wall of the aorta. The embodiment shown in FIG. 3 and FIG. 4 includes a retractable blade guard 33 which is inserted into the distal end 16 of the cannula. The blade guard 33 is adapted to slideably receive the cutting blade 30. During use, the blade guard moves when pressed against the aorta to allow the blade to cut through the wall of the aorta, and then the blade guard repositions to prevent the blade from cutting. In the embodiment shown in FIG. 3 and FIG. 4, the proximal end 34 of the cutting blade guard is coupled to the distal end of a spring 35. The proximal end of the spring 36 is coupled to the inner surface of the cannula. When the spring is at its compressed length, as depicted in FIG. 3, the retractable blade guard is retracted exposing the cutting blade 31. When the spring is at its extended length, the retractable blade guard covers the sharpened tip of the cutting blade as depicted in FIG. 4.

The cardioplegia occluder depicted in FIG. 3 and FIG. 4 is placed on the aorta, upstream from the brachiocephalic artery. When pressure is applied to the cardioplegia occluder, the surface of the aorta pushes on the retractable blade guard, compressing the spring and exposing the sharpened tip of the cutting blade which cuts through the wall of the aorta to create an incision for introduction of the distal end of the cannula. The distal end of the cannula, with the occluder in a contracted condition, is introduced through the incision made by the cutting blade. Such an embodiment can be introduced through a site that is a maximum of 18 French. During insertion, aspiration can be effected through the aspiration lumen to remove intravascular debris or air introduced into the aorta during incision. The curved distal end of the cannula is positioned at the desired location inside the aorta, and the occluder is expanded by introducing fluid through the lumen 7. Once the occluder is fully expanded, blocking the blood supply to the aorta in the region distal to the occluder, cardioplegia solution may be introduced through the infusion port to the region upstream from the occluder to stop the heart. Cardiac surgery, may then be performed. Alternately, negative pressure can be applied to the proximal end of the aspiration lumen to remove cardioplegia and embolic debris from the aorta. In embodiments that do not include a cutting blade, the incision is made manually, and the distal end of the cannula is inserted as previously described. Following surgery, the flow of cardioplegia solution is stopped, negative pressure is applied to the lumen, the occluder contracts, the cardioplegia occluder is removed through the incision initially created for its insertion and the incision is closed.

FIG. 5 shows another embodiment where a blood cannula 56 has a channel 57 located laterally that is adapted to receive a cardioplegia occluder 58. When the occluder 20 is expanded inside the aorta 41, cardioplegia solution can be delivered upstream of the occluder through the infusion port 59. This embodiment is one example of an integrated configuration of a blood cannula and a cardioplegia occluder for use in a "one-stick" application, meaning that only one incision need be made.

Human anatomy including the rib cage with deployed cardioplegia occluder is depicted in FIG. 6. The cardioplegia occluder 1 is disposed through a chest access port 40 and thereafter enters the aorta 41 behind the sternum 45 at a location 42 upstream from the brachiocephalic artery 43. The rib cage is depicted generally by numeral 44. The cardioplegia occluder 1 is shown deployed within the aorta 41. The concept of port access allows a surgeon to enter the aorta via a port for a minimally invasive approach. By accessing the aorta directly, the device is deployed without the need for visual guidance, e.g., fluoroscopy, echocardiography. This device would obviate the need for a sternotomy procedure which is generally associated with conventional coronary artery bypass grafting surgery.

The cardioplegia occluder may be constructed to sit in either direction once introduced in the aorta by varying the location of the infusion port. In one embodiment, depicted in FIG. 7, an L-shaped cardioplegia occluder 1 is constructed to sit inside the aorta with occluder 20 downstream from the incision site 55, with the occluder 20 mounted distal to, or downstream from, the infusion ports 5. The cardioplegia occluder optionally includes seating bumps 50 to enhance sealing with the interior of the aorta. In another embodiment shown in FIG. 7A, a J-shaped cardioplegia occluder 1 is constructed to sit inside the aorta 41 so that the occluder 20 is mounted proximal to, but still downstream from, the infusion port 5 which is located at the distal opening 14 of the cannula. These cardioplegia occluders can be inserted through a pre-slit section of the aorta, or a cutting blade can be mounted on the distal end of the cannula and advanced through the aortic wall.

An integrated, multiple component port access cardioplegia occluder is depicted in FIG. 8. The system includes a cutting blade 60 having a pre-shaped configuration 61, a sharp tip 62, and position limiters 63. The cannula 3 includes a suture plate 70, a kink-resistant shaft 71, an opening 72 to receive cardioplegia infusion solution into the cardioplegia lumen and a hemostasis valve 73. The balloon cannula 80 includes an occluder 81, an inflation port 82 and a lumen 83 and is adapted to receive a filter mesh 500 through the lumen. The cannula 3 is adapted to receive the cutting blade 60 through the infusion port 72, and to receive the occlusion device 80 through the hemostasis valve 73. In use, a port access point or window is opened on the patient's chest.

Tissue from the port to the aorta is dissected. The cutting blade and cannula are advanced through the aortic wall. A purse string suture(s) may be required to aid in wound closure and to secure the device. At the desired location, the cutting blade is advanced through the aortic wall and the cannula is pushed with the cutting blade. Once inside the vessel, the cannula is secured and the cutting blade is removed. At this point, the occluder (and any filter) may be advanced and expanded. Cardioplegia and other fluids may then be circulated through the cardioplegia lumen.

The distal end of the cannula may assume various designs to assist the surgeon in positioning the cardioplegia occluder in the aorta. In one embodiment, depicted in FIG. 9, a lumen 90 is adapted to receive the cutting blade 110. The cutting blade lumen 90 enters the distal region of the cannula 3 at an angle. A substantially straight cutting blade 110 is introduced into the lumen 90 so that the sharp tip 111 of the blade protrudes beyond the opening 91 at the distal end of the cutting blade lumen. In use, this embodiment allows for a single stick motion whereby the cutting blade pierces the wall of the aorta creating an incision and the distal end of the cannula, with the occluder in a collapsed condition, is advanced through the incision. A flange 100 mounted on the cannula presses against the exterior surface of the aortic wall preventing further movement of the cannula into the vessel at the point where the cannula is positioned in the desired location within the aorta. The cutting blade is then retracted and the occluder 20 is expanded to block the flow of arterial blood. An advantage of this embodiment is that it has no moving parts other than the retractable cutting blade. In other embodiments, the cutting blade lumen extends distally from the proximal end of the cannula.

The embodiment depicted in FIG. 10 has a retractable cutting blade 112 slideably inserted into a cutting blade lumen 92 within the distal end of the cannula 3. The proximal end 114 of the cutting blade is coupled to a spring 120 and to an activator line 130. The activator line can be made of material such as wire. The proximal end of the spring is coupled to a stop 121 formed inside the cutting blade lumen. When the activator line 130 is pulled, the spring 120 compresses and the sharp tip 111 of the cutting blade 112 is retracted into the distal end of the cutting blade lumen 92 which then serves as a blade guard. When the activator line 130 is released, the spring 120 expands and the sharp tip 111 of the device is exposed to allow incision into a vessel. The embodiment also includes infusion ports 101 for introduction of cardioplegia solution upstream from the occluder 20.

FIG. 10A shows another embodiment where the blade guard is a retractable obturator 140. In this embodiment, the distal end 114 of the cannula is sharp, thus forming the cutting blade, and is used to create the initial incision into the aorta. The retractable obturator 140 is slideably received through the cutting blade. In the embodiment of FIG. 10A, the retractable obturator is coupled on its proximal end to a spring 120 and to an activator line 130. The spring is coupled on its proximal end to a stop 121 formed inside the cutting blade lumen. During use, the obturator can be moved by pulling on the activator line to expose the sharp distal end 114 of the cannula which is used to cut through the wall of the aorta. When the activator line is released, the obturator moves back to prevent the blade from cutting.

Figure 12:
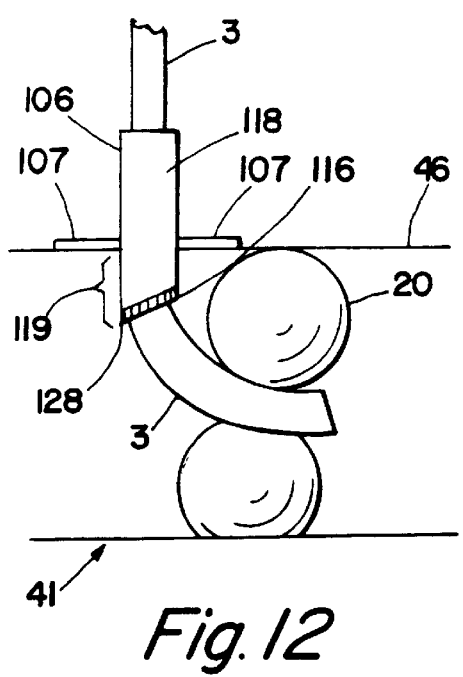
FIG. 12 shows the embodiment of FIG. 11 where the balloon cannula and the expanded occluder have advanced beyond the distal end of the flange sleeve and into the vessel.

FIG. 11 depicts a flange sleeve 105 adapted to receive the cannula. In some embodiments, the flange sleeve is substantially cylindrical. In other embodiments, the flange sleeve may have a different shape on cross-section such as square, rectangular, oblong or other shapes. The flange sleeve has a sharpened distal end 116 adapted to cut through the wall of the aorta, an inner surface 108, an outer surface 109, a proximal end 117, a distal end and a longitudinal center axis. The lumen 118 of the flange sleeve 106 runs along the longitudinal center axis and communicates with openings at the proximal 117 and distal 116 ends of the sleeve. This embodiment also includes a flange stop 107, with a top surface 125, which faces the proximal end of the flange sleeve, and a bottom surface 126, which faces the distal end 116 of the flange sleeve. The flange stop 107 is mounted on the flange sleeve. The perimeter of the flange stop can be substantially circular, or shaped so that a region of the perimeter includes a protrusion or notch in the plane of the flange stop, where the protrusion or notch indicates the direction of the tip 128 of the cutting edge 116 of the flange sleeve. In the embodiment of FIG. 11, the portion of the flange sleeve distal to the bottom surface 126 of the flange stop 125 and proximal to the cutting edge 116 at the distal end of the sleeve is of a length 119 that will position the cutting edge 116 of the flange sleeve at a predetermined depth inside the aorta when the bottom surface 126 of the flange stop contacts the outer surface 46 of the aorta thus preventing further movement of the flange sleeve into the aorta. FIG. 11 shows the cannula 3 retracted inside the lumen of the flange sleeve. When in the retracted state, the occluder 20 is in a contracted condition. When in use, the cutting edge 116 of the flange sleeve is pressed into the outer surface of the wall of the aorta 46, while the cannula 3 is in the retracted state and the occluder 20 is in a contracted condition. The cutting edge 116 of the flange 105 is advanced into the aorta until the flange stop 107 contacts the outer surface of the wall of the aorta 46. In the next step, as depicted in FIG. 12, the cannula 3 is advanced beyond the cutting edge 116 of the flange until the distal end of the cannula is situated at the predetermined position within the aorta 41. The occluder 20 is then expanded to prevent blood flow downstream in the aorta. In this embodiment, the distal end of the cannula is semi-rigid and preformed to assume a substantially curved condition when released from the flange. When retracted inside the flange, as depicted in FIG. 11A, the semi-rigid distal end of the cannula 3 generally conforms to the shape of the flange sleeve lumen which is straight.

Figure 13:
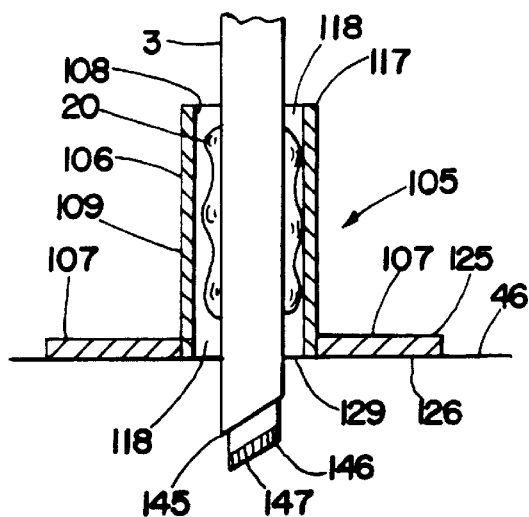
FIG. 13 shows lateral cross-section of an embodiment with an exposed cutting blade and a cannula with a collapsed occluder positioned inside the flange sleeve.
Figure 13A:
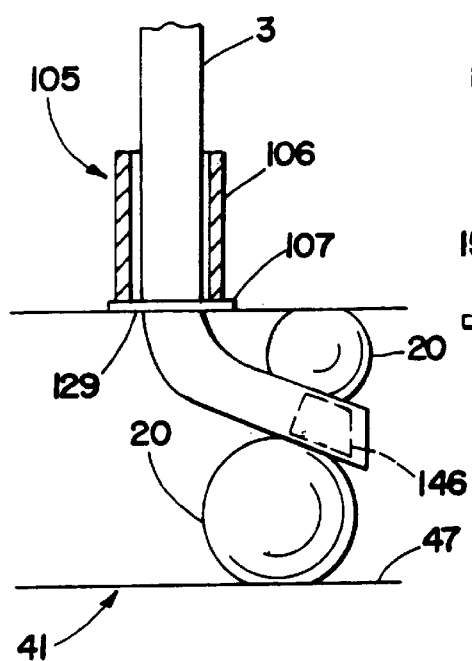
FIG. 13A shows the embodiment of FIG. 13 where the cannula and the expanded occluder have advanced beyond the end of the flange sleeve and into the vessel, and the cutting blade is retracted inside the distal end of the cannula.

In another embodiment, depicted in FIG. 13, the flange 105 includes a flange sleeve 106 with an inner surface 108, an outer surface 109, a proximal end 117, a distal end 129, and a longitudinal center axis. The lumen 118 of the flange sleeve 106 runs along the longitudinal center axis and communicates with openings at the proximal 117 and distal 129 ends of the sleeve. This embodiment also includes a substantially flat flange stop 107, with a top surface 125, which faces the proximal end of the flange sleeve, and a bottom surface 126 which is flush with the distal end 129 of the flange sleeve. The bottom surface 126 of the flange stop is adapted to press against the outer surface 46 of the aorta. FIG. 13 also shows the cannula 3 partially retracted inside the lumen 118 of the flange sleeve. When in the retracted state, the occluder 20, which is disposed about the distal region of the cannula 3, is in a contracted condition. In this embodiment, the distal end 145 of the cannula includes a cutting blade lumen having a retractable cutting blade 146 with a sharpened cutting edge 147 at its distal end. The cutting blade 146 slideably inserts inside the cutting blade lumen and protrudes beyond the distal end 145 of the cannula 3. When in use, the flange 105 is positioned with the bottom surface 126 of the flange stop 107 pressing against the outer surface of the wall 46 of the aorta and the cannula 3 and cutting blade 146 are in the retracted state inside the lumen 118 of the flange sleeve 106 proximal to the distal opening 129 of the sleeve. The cannula 3 and the cutting blade 146 are pushed through the lumen 118 of the flange sleeve beyond the distal opening 129 so that the sharpened cutting edge 147 of the cutting blade 146 cuts into the wall of the aorta forming an incision as depicted in FIG. 13. Once the incision is formed, the cannula 3 is advanced beyond the distal opening 129 of the flange sleeve 106, as depicted in FIG. 13A, so that the distal end of the cannula and the occluder 20 are introduced into the aorta 41 to the predetermined depth and position. In this embodiment, the semi-rigid distal end of the cannula is preformed to assume a curved shape once it is released from the lumen of the flange. As the cannula is advanced beyond the distal opening 129 of the flange into the aorta, the cutting blade 146 slideably retracts within the cannula so that is does not protrude beyond the distal opening 146 of the cannula. Once the cutting blade has been deployed to create the initial incision, it is desirable to retract it inside the cannula or otherwise guard the sharpened tip so that the sharp edge of the blade does not scrape or cut the inner surface 47 of the wall of the aorta opposite the incision site. The occluder 20 may then be expanded to occlude arterial flow downstream in the aorta.

Figure 14:
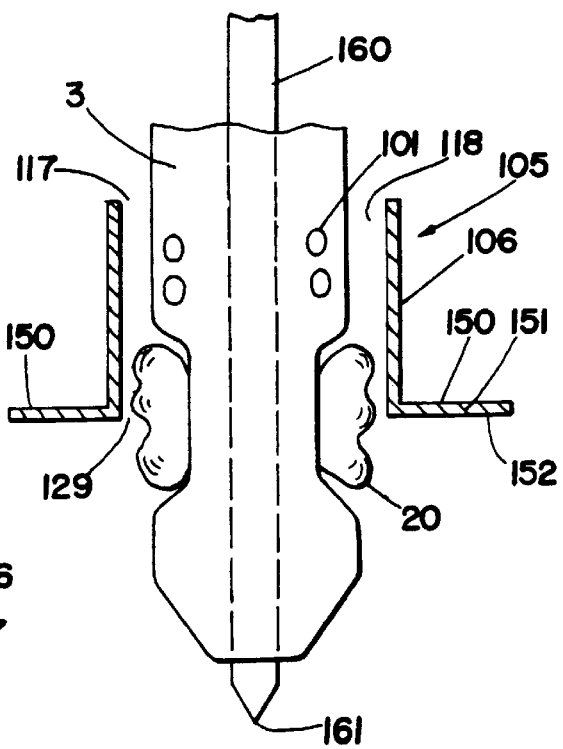
FIG. 14 depicts a lateral cross-section of an embodiment partially inserted into a vessel where the embodiment includes a detachable intermediate flange containing a cannula with a collapsed occluder and an exposed cutting blade.
Figure 14A:
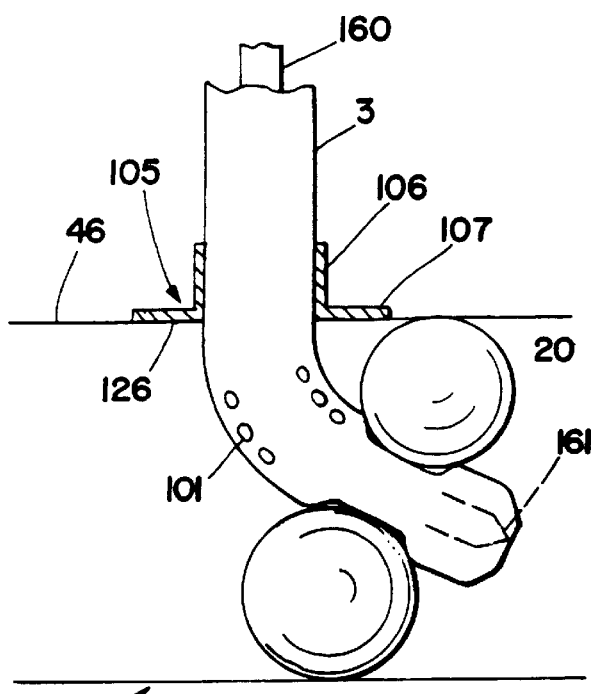
FIG. 14A depicts the embodiment of FIG. 14 where the cannula and the expanded occluder have advanced beyond the end of the flange and into the vessel and the cutting blade is retracted.

In another embodiment, depicted in FIG. 14, the flange 105 includes a flange sleeve 106 with a proximal end 117, a distal end 129, and a longitudinal center axis. The lumen 118 of the flange sleeve 106 runs along the longitudinal center axis and communicates with openings at the proximal 117 and distal 129 ends of the sleeve. This embodiment also includes a substantially flat tear-away flange stop 150, with a top surface 151, which faces the proximal end of the flange sleeve, and a bottom surface 152, which is flush with the distal end 129 of the flange sleeve. The tear-away flange stop 150 is disposed about the outer surface of the flange sleeve 106 at the distal end 129 of the sleeve. The bottom surface 152 of the tear-away flange stop is adapted to press against the outer surface 46 of the aorta to limit the initial insertion depth into a vessel. FIG. 14 also shows the cannula 3 partially retracted inside the lumen 118 of the flange sleeve. When in the retracted state, the occluder 20 is in a contracted condition. A cutting blade 160 is adapted to slideably insert inside a lumen within the cannula. In this embodiment, the distal end 161 of the cutting blade is sharpened 161 to cut through the wall of the aorta. When in use, the cannula 3, with the sharpened cutting edge 161 of the cannula insertion device 160 exposed, is advanced through the wall of the aorta until the bottom surface 152 of the tear-away flange stop 150 presses against the outer surface of the wall of the aorta. As depicted in FIG. 14A, the cutting blade 160 is then retracted within the distal end of the cannula 3 as the tear-away flange is removed and the cannula is advanced into the lumen of the aorta until the bottom surface 126 of the permanent flange stop 107 presses against the outer surface 46 of the wall of the aorta. By this process, the distal end of the cannula and the occluder 20 are introduced into the aorta 41 to the desired depth and position. In this embodiment, the semi-rigid distal end of the cannula is preformed to assume a curved shape once it is released from the lumen of the flange. The occluder 20 may then be expanded to occlude arterial flow downstream in the aorta.

Figure 15:
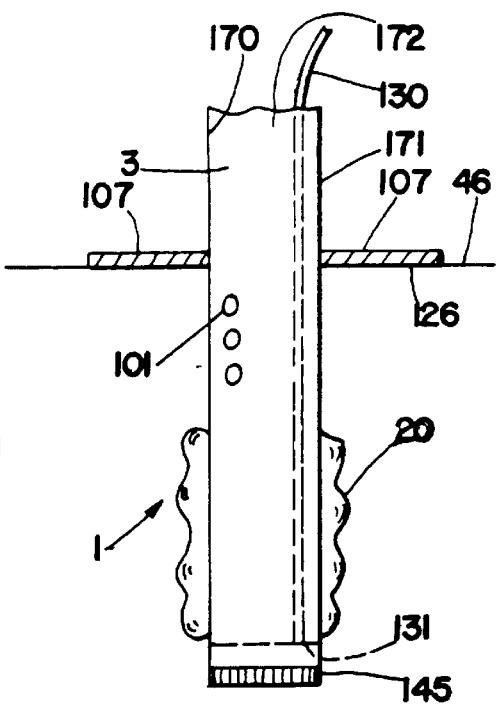
FIG. 15 shows a lateral cross-section of an embodiment having flange mounted on the cannula and a steering wire coupled to the distal end of the cannula where the occluder is in a collapsed condition.
Figure 15A:
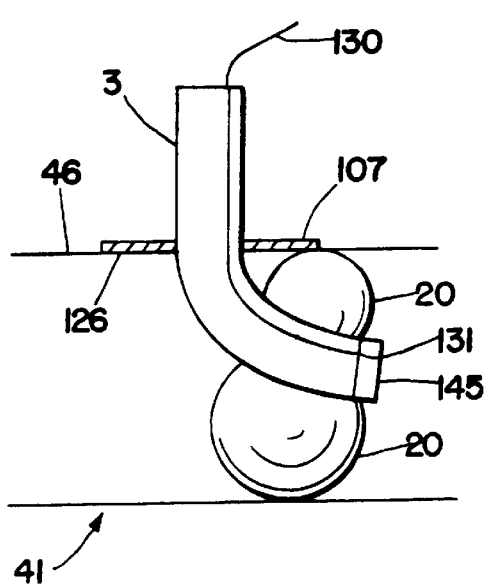
FIG. 15A shows the embodiment of FIG. 15 where the steering wire has been manipulated to curve the distal end of the cannula and the occluder is in an expanded condition.

As described previously, in certain embodiments, the distal region of the cannula may be preformed to a desired shape to allow the cannula to be positioned at the desired depth and orientation within the aorta. In other embodiments, the distal region of the cannula may be mechanically activated by an occluder aligner to allow proper positioning of the occluder within the aorta. FIG. 15 depicts an embodiment with one form of occluder aligner that includes a cannula 3 with an inner surface 170, an outer surface 171, a proximal end (not shown), a distal end 145 and a longitudinal center axis. The lumen 172 of the cannula runs along the longitudinal center axis and communicates with openings at the proximal and distal 145 ends of the cannula. The cannula also includes a flange stop 107 disposed about the outer surface 171 of the distal region of the cannula. The occluder aligner of this embodiment includes a steering wire 130 carried by the cannula, displaced from the center axis of the cannula and attached on a first end 131 in the distal region of the cannula, in the case of this embodiment, to the inner surface 170 of the distal region. When in use, as depicted in FIG. 15 and FIG. 15A, the cardioplegia occluder 1 is advanced through an incision in the wall of the aorta 41 until the bottom surface 126 of the flange stop 107 presses against the external surface of the wall 46 of the aorta. At this point, as shown in FIG. 15, the occluder 20 is in a contracted condition. The steering wire 130 is then manipulated, as depicted in FIG. 15A, to move the distal end of the cannula into a curved condition, so that the distal opening 145 of the cannula points downstream within the aorta 41. In one embodiment, the occluder is aligned by pulling on the steering wire. In another embodiment, the steering wire is fabricated from a material that shortens upon application of a predetermined electrical input. When this predetermined electrical input is applied to the steering wire, the wire shortens by a predetermined length, pulling the distal end of the cannula into the predetermined position. In another embodiment, a control circuit containing a memory storage device controls the electrical input to be applied and the timing of the application and discontinuance of the electrical input, so that the change in length of the wire may be programmed. Once the occluder 20 is properly aligned within the aorta, the occluder may be expanded to occlude arterial flow downstream in the aorta.

Figure 16:
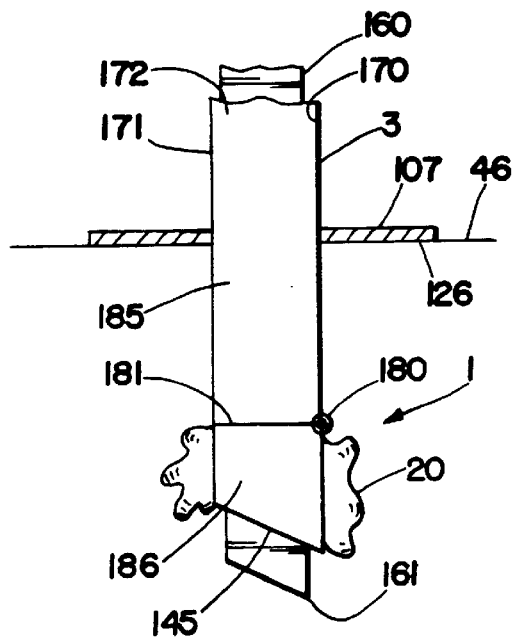
FIG. 16 depicts a lateral cross-section of an embodiment having flange and a hinged distal cannula region where the hinge is in a closed condition and the occluder is in a collapsed condition.
Figure 16A:
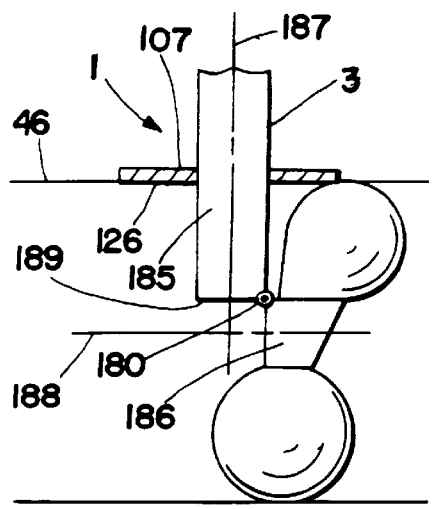
FIG. 16A depicts the embodiment of FIG. 16 where the hinge is in an open condition creating an infusion port, and the occluder is in an expanded condition.

FIG. 16 depicts another cannula that is mechanically activated to facilitate proper positioning of the occluder within the aorta. This embodiment includes a cannula 3 with an inner surface 170, an outer surface 171 and a longitudinal axis. The cannula is divided into two segments, a proximal portion 185 and a distal portion 186, flexibly coupled to one another. In the embodiment shown in FIG. 16, the flexible coupling is a hinge 180. In the closed condition, as depicted in FIG. 16, the distal end of the proximal portion 185 and the proximal end of the distal portion 186 align at a circumferential region 181, so that the cannula assumes a substantially cylindrical shape. In other embodiments, the cannula on cross-section can be rectangular, square, oblong or other shapes. In the open condition, as depicted in FIG. 16A, the distal portion 186 rotates about the hinge so that the longitudinal axis 188 of the distal portion 186 is about a 90° angle to the longitudinal axis 187 of the proximal portion 185. In the closed condition, the lumen 172 of the cannula runs along the longitudinal center axis and communicates with openings at the proximal and distal 145 ends of the cannula. The cannula also includes a flange stop 107 disposed about the outer surface 171 of the distal region of the cannula, and a cutting blade 160 which slideably inserts within the lumen 172 of the cannula when the cannula is in the closed condition. When in use, as depicted in FIG. 16, the cutting blade 160 protrudes beyond the distal end 145 of the cannula 3 which is in the closed condition with the occluder contracted. The presence of the cutting blade in the lumen of the cannula helps maintain the cannula in a closed position. The sharp distal end 161 of the cutting blade 160 is advanced through the wall of the aorta 41 creating an incision, and the cannula 3 is advanced into the aorta until the bottom surface 126 of the flange stop 107 presses against the external surface of the wall 46 of the aorta. The cannula insertion device is then removed causing the hinge to open as depicted in FIG. 16A, and the cannula assumes the open condition with the distal portion 186 of the cannula pointing downstream in the aorta. In some embodiments (not shown), the cannula opens with the assistance of a spring-loaded hinge. The occluder 20 may then be expanded to occlude arterial flow downstream in the aorta. Cardioplegia solution may then be introduced through the proximal portion 185 of the cannula for delivery through the fluid port 189 upstream of the occluder.

Figure 17:
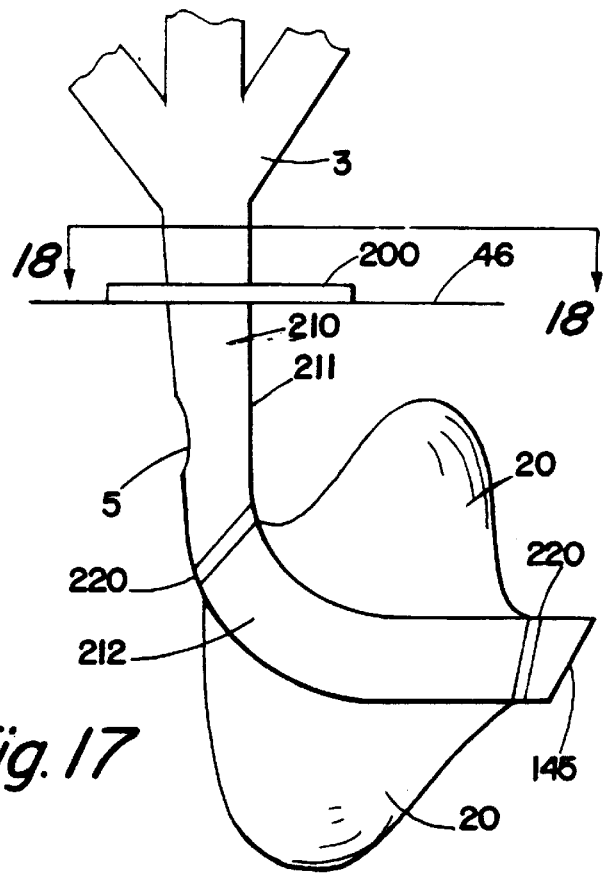
FIG. 17 is a lateral cross-section of an embodiment having a flange with a directional indicator, a cannula with three lumens, a cutting blade and radiopaque marker bands, where the cannula is inserted through an 18 French incision.
Figure 18:
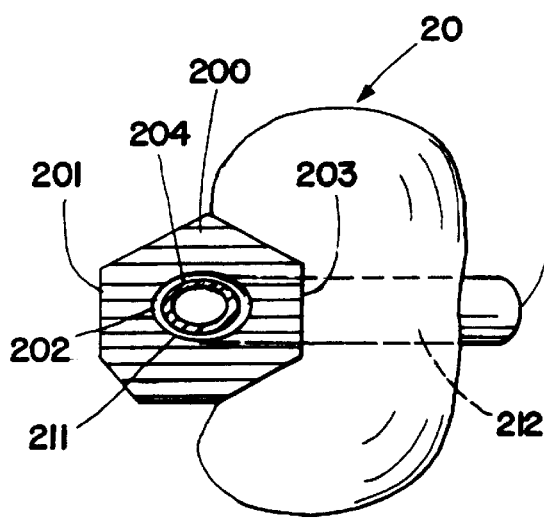
FIG. 18 is a top elevation of the embodiment of FIG. 17 showing the alignment of the directional indicator of the flange with the distal region of the cannula.

FIG. 17 depicts an embodiment where the distal region of the cannula 3 is tapered 210. The embodiment of FIG. 17 also shows, a curved region 212, distal to the tapered region. In this embodiment, the tapered region, on cross-section, as depicted in FIG. 18, is substantially elliptical. As also depicted in FIG. 18 from a top elevation, the long diameter of the ellipse of the tapered region cross-section lies directly above the curved region 212 of the cannula. This embodiment also includes a flange which is slideably received by the cannula. The flange in this embodiment has a directional indicator. As can be seen in the top elevation of FIG. 18, the flange assumes the shape of a polygon. In other embodiments, the flange can be other shapes such as rectangular, oblong, or triangular. The flange includes a hole 204 that is substantially elliptical, having an inner circumference 202. The hole is placed off-axis from the center of the polygon. The long diameter of the elliptical hole is perpendicular to the directional edge 203 of the polygon perimeter of the flange. The distance from the directional edge 203 to the nearest point on the inner circumference of the hole 204 is greater than the distance from the edge 201 opposite the directional edge to the point on the inner circumference nearest that opposite edge. The inner circumference 202 of the hole in the flange is greater than the circumference of the outer surface 211 of the distal end of the tapered region 210 of the cannula, but less than the circumference of the outer surface 211 of the proximal end of the tapered region 210 of the cannula. The flange is disposed about the tapered region of the cannula. The distal end of the tapered region is adapted to slideably insert in the hole of the flange and the proximal portion of the tapered region slideably inserts in the flange up to the location where the circumference of the outer surface 211 of the tapered region of the cannula is substantially equal to the inner circumference 202 of the hole in the flange, at which location the flange is no longer free-floating, and locks into position on the tapered region. The tapered condition of the cannula assists in sealing the cannula to the flange. Since the hole 204 of the flange and the cross-section of the tapered region are both elliptical in shape, the flange will always be oriented in the same position on the cannula when it locks into place; that is, the directional edge 203 will always point toward the curved region 212 of the cannula, which assists the surgeon in knowing which way the occluder is pointing in the aorta. In other embodiments, the tapered region 210 and the hole 204 of the flange may assume other shapes on cross-section, such as rectangular or triangular. In some embodiments, the directional edge is identified by a specific color. The embodiment of FIG. 17 also includes marker bands 220 around the outer surface 211 of the curved region 212 of the cannula in the most proximal and most distal locations where the occluder 20 contacts the cannula. The marker bands are made of radiopaque material such as metal-polymeric alloy so that the surgeon can identify the position of the occluder.

Figure 19:
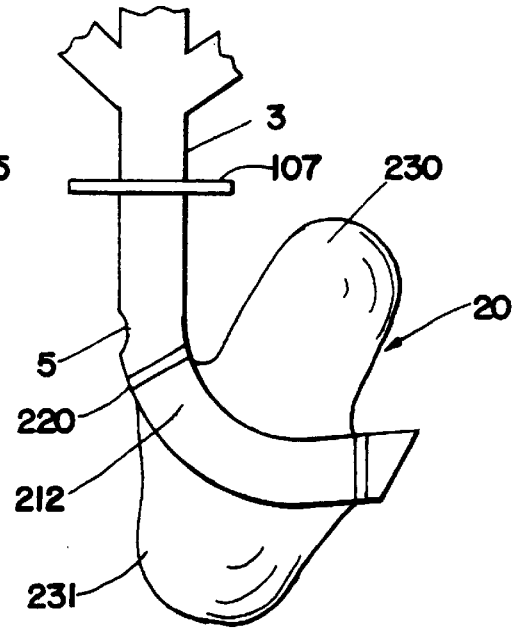
FIG. 19 shows a lateral elevation of an embodiment with radiopaque marker bands and an occluder asymmetrically disposed about the distal end of the cannula.
Figure 19A:
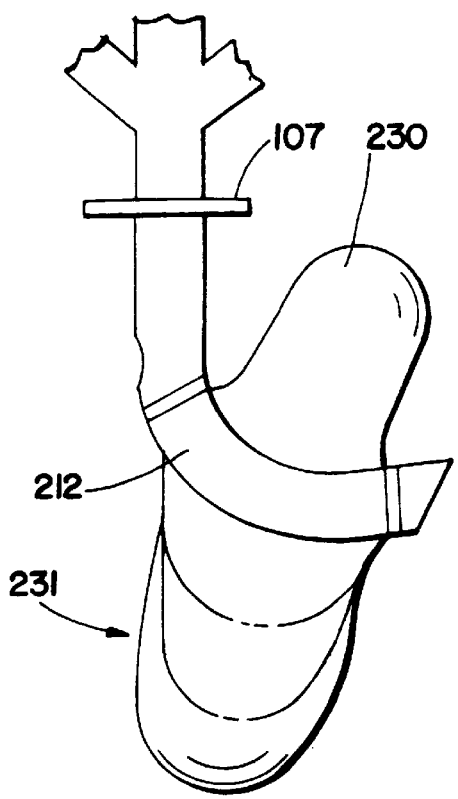
FIG. 19A shows the embodiment of FIG. 19 where the bottom region of the asymmetrically disposed occluder is preferentially expanding when compared to the top region.
Figure 20:
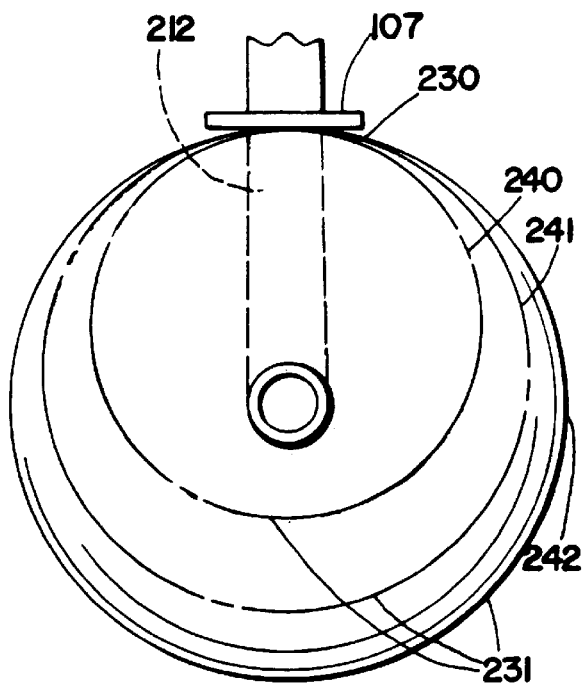
FIG. 20 shows the front view of the embodiment of FIG. 19, showing the preferential expansion of the bottom region of the occluder as the occluder goes from a collapsed condition to an expanded condition.

For the cardioplegia occluder to function properly, the occluder must be adapted to occlude aortas of varying diameters. Moreover, the internal surface of the aorta may have varying surface features creating additional challenges to fashioning occluders that will conform to the topography of the inner surface of the vessel and form a complete seal. The challenge of occluding aortas of varying diameter is further compounded in embodiments with fixed flanges. To overcome such obstacles, in certain embodiments, the occluder is a balloon having a first region of first expansion capacity and a second region of second expansion capacity where the first expansion capacity is greater than the second expansion capacity. During use, the second region expands preferentially and to a greater extent than the first region. These embodiments can thus compensate for insertions where the distal end of the cannula does not lie directly in the center of the aorta and by thus compensating creates effective sealing. In some embodiments, the varying expansion capacity is created by forming the first region from a flexible material of different thickness that the flexible material used to create the second region. In other embodiments, the first region is of a different modulus (durometer) than the second region. In other embodiments, the occluder is adapted to occlude aortas of varying diameters by asymmetrically mounting the balloon on the distal region of the cannula. The embodiment shown in FIG. 19, which demonstrates this last case, has an occluder 20 that is a preformed asymmetric balloon where the "long" side 230 has less capacity to expand than does the "short" side 231. The flange 107, as described in previous embodiments, will hold the curved portion 212 of the cannula at a predetermined distance below the region of the wall of the aorta closest to the flange. In aortas of varying diameters, the distance between the curved portion of the cannula and the wall opposite the flange will necessarily vary. To facilitate occlusion in these varying conditions, the short side 231 has a greater capacity for expansion, as depicted in FIG. 19A, than does the long side 230, so that upon inflation by a common fluid source, the short side 231 will preferentially expand over the long side 230. FIG. 20 is a front elevation of the embodiment of FIG. 19A showing how the short side 231 preferentially expands over the long side 230 to occlude aortas of smaller 240, intermediate 241, and larger 242 diameters even though the flange 107 fixes the depth of the cannula within each vessel.

Figure 21:
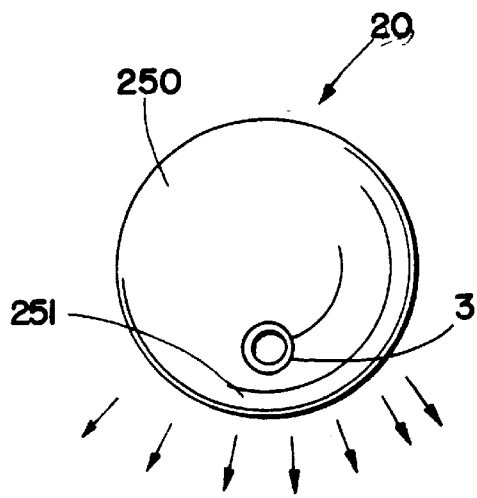
FIG. 21 shows an embodiment of an occluder that is an asymmetric polyurethane balloon.
Figure 22:
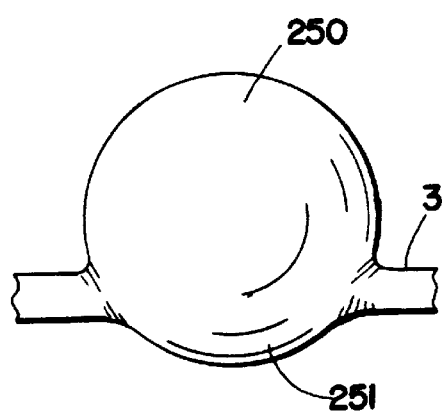
FIG. 22 is a lateral view of the embodiment of FIG. 21.

There are several methods to achieve varying capacities for expansion in given regions of the balloon occluder. Typically, it is desired to achieve a preferential expansion zone as depicted in FIG. 21 where a balloon occluder 20 is asymmetrically disposed about a cannula, and the occluder has a region 251 that has a greater capacity to expand when compared to another region 250. FIG. 22 is a lateral elevation of the embodiment of FIG. 21. These asymmetric balloons, which can be fabricated from polyurethane, typically inflate to a more symmetric shape as depicted in FIG. 23, where varying balloon wall thickness is used to control expansion characteristics. A thin region 252 of the balloon will expand first, reaching a certain level of strain/elongation 252', then a thicker region 253 will stretch to its expanded condition 253'. The expanded balloon is symmetrically disposed about the cannula.

FIG. 24 depicts another embodiment where balloon materials with differing expansion capacities are used to create a balloon which is asymmetric upon expansion. In this embodiment, a region of soft material 255, e.g., one of lower modulus and usually lower durometer, expands more freely 255' than does a region of harder material 254, e.g., one of higher modulus and usually higher durometer, which expands less freely 254'.

It is also important that the occluder not prolapse at the locations where the occluder surface is not in contact with the inner surface of the aorta when the occluder is expanded. Such prolapse can cause the occluder to not seal properly. Increasing thickness in these non-contact regions can reduce the risk of prolapse and can otherwise control occluder length and shape. FIG. 25 depicts an embodiment where the balloon occluder has regions where the balloon material is thin 256 and sidewall regions where the balloon material is thick 257. When the balloon expands, the thin regions 256, which ultimately contact the inner wall of the aorta, expand more freely to their expanded condition 256'. The thick sidewall regions 257, which do not contact the inner surface of the aorta and are thus at risk of prolapse, expand less freely to their expanded condition 257' and, due to their thickness, are more robust. The overall average balloon length from location 260 to location 261 is reduced from the length that would otherwise result if the sidewalls were not made of thicker material. Thus, a prolapse-resistant balloon occluder with a small "footprint" (area of contact on the distal region of the catheter), can be fabricated. This small footprint occluder, when used with the substantially rigid cannula allows the occluder to isolate the ascending aorta from peripheral vasculature without substantial migration of the occluder into the ascending aorta.

Figure 26:
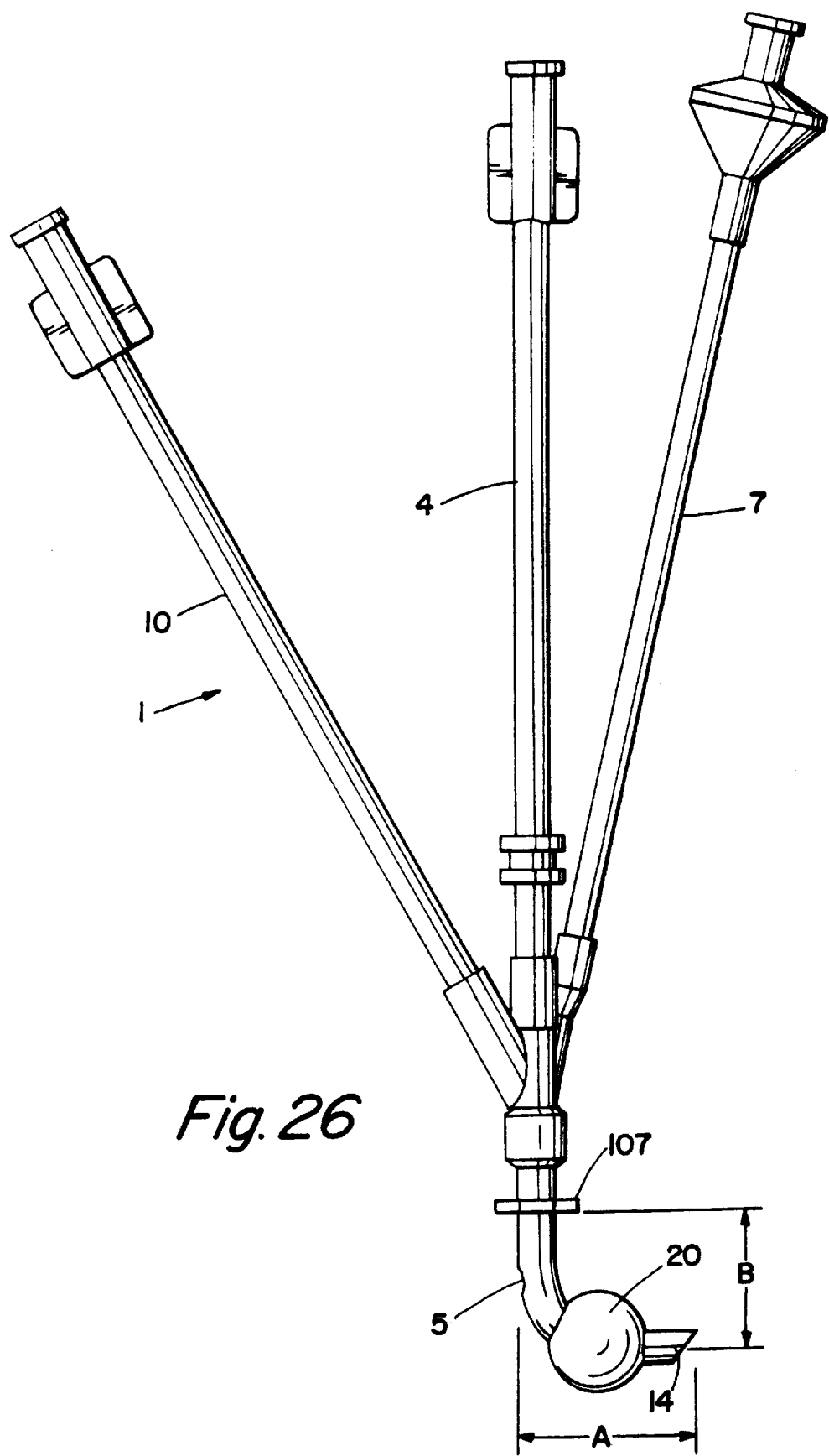
FIG. 26 depicts an embodiment with a three-lumen cannula having a curved distal cannula region.

FIG. 26 depicts an embodiment of a cardioplegia occluder 1 where the substantially rigid cannula 3 includes three lumens 4, 10 and 7, a flange 107 and a spherical occluder 20. The infusion port 5 is shown proximal to the occluder. Certain embodiments of the cannula are made of clear polycarbonate acrylic, ABS or stainless steel. In one embodiment, the region of the cannula proximal to the flange is made of clear polycarbonate, acrylic or ABS, and the region of the cannula distal to the flange is made of stainless steel. The plastic region and the stainless steel region are insert-molded at the junction. In the preferred embodiment, (i) the length of the cannula from the proximal end to curved portion of the distal region is in the range of 5–10 inches, most preferably 7.5 inches, (ii) the width of the distal region from the beginning of the point of curvature to the distal end (distance A in FIG. 26) is in the range of 0.25–0.75 inches, most preferably 0.45–0.50 inches; and (iii) the distance between the flange and the distal end (distance B in FIG. 26) is the range of ⅜ inch to 1.0 inch, and most preferably ¾ inch. FIG. 27 is a front elevation of the embodiment of FIG. 26. FIG. 28 is a lateral cross-section of the embodiment of FIG. 27 shown through section line 28—28. Here, the pathways of the three lumens are depicted in greater detail. The lumen 7 is shown communicating with the inflation port 8 which opens into the chamber of the occluder 20. The cardioplegia lumen 4 is shown communicating with the infusion port 5 which opens into the region of the aorta upstream of the occluder. The aspiration lumen 10 also communicates with the infusion port. FIG. 29 is a front elevation of the distal region of the cannula 3 of the embodiment of FIG. 26 with the occluder removed. In this figure, the closed distal end 14 of the cannula can be seen. FIG. 30 is a top elevation of the embodiment of FIG. 29, showing the relative locations of the lumen 7 that is used to inflate/deflate the occluder, the cardioplegia lumen 4 and the aspiration lumen 10 as they enter the region of the cannula just proximal to the flange. FIG. 31 is a lateral view of the embodiment of FIG. 29 with a partial cross-section of the curved region of the cannula. The occluder mounting zones 270 are shown on either side of the cross-section region.

This view shows the relationship between the infusion port 5, shown proximal to the occluder mounting zones, and the inflation port 8 which opens in the region between the occluder mounting zones and thus communicates with the chamber of the occluder. FIG. 32 is a bottom elevation of the embodiment of FIG. 29. FIG. 33 is a back elevation of the embodiment of FIG. 29, again showing the relative locations of the infusion port 5 and the inflation port 8. FIG. 34 is a lateral cross-section of the embodiment of FIG. 29 shown through the section line 34—34.

Figure 35:
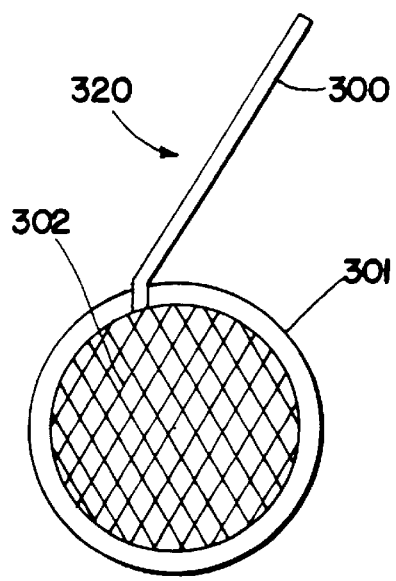
FIG. 35 is an embodiment showing a self expanding occluder with a Nitinol frame, a balloon seal and an impermeable membrane.
Figure 36:
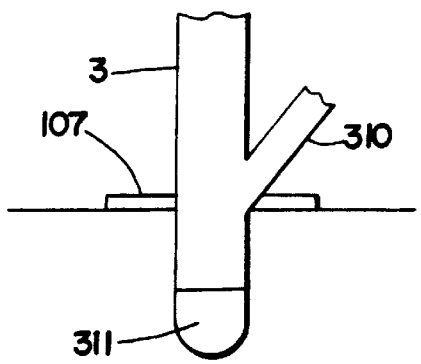
FIG. 36 shows an embodiment of a cannula poised to receive the occluder of FIG. 35.
Figure 37:
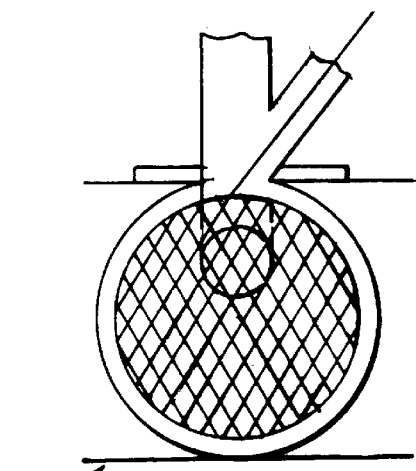
FIG. 37 shows the occluder of FIG. 35 inserted through the side port of the cannula of FIG. 36.

FIG. 35 is an embodiment showing a self-expanding occluder 320 with a hollow Nitinol frame 300, a balloon seal 301 and a fluid-impermeable membrane 302. The occluder is an annular-shaped balloon having an inner circumference and an outer surface and a flexible, fluid-impermeable membrane bonded to the outer surface of the balloon and covering the area circumscribed by the inner circumference of the annular balloon. FIG. 36 shows a cannula 3 with an occluder side port 310, a flange stop 107 and a fluid port 311. FIG. 37 shows the self-expanding occluder 320, which has been inserted into the occluder side port 310 while in a collapsed condition after the distal region of the cannula has been inserted into the aorta 41. Once properly positioned, the balloon seal 301 is inflated through the hollow Nitinol frame 300 and the occluder expands, occluding the vessel.

Figure 38:
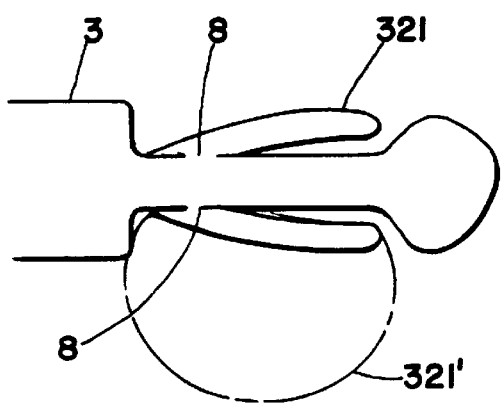
FIG. 38 shows an embodiment of an occluder where the balloon has excess balloon material.

In some applications it is desirable to provide occluder constructions with enhanced stability and/or increased expandability. FIG. 38 depicts an overlapping balloon occluder 321, fabricated with excess balloon material, which allows the occluder to inflate to a larger size while stretching and elongating to a lesser extent. A portion of the occluder in its expanded condition 321' is also shown. This embodiment may also include thicker regions of the balloon wall to control the inflation profile.

Figure 39:
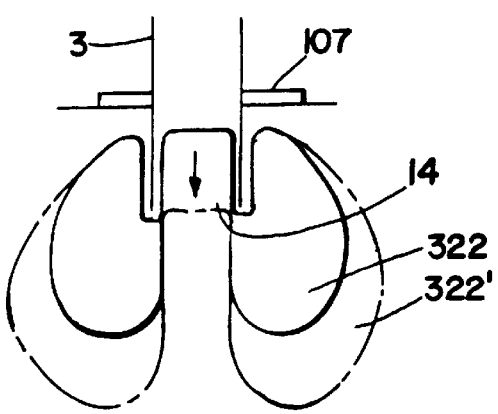
FIG. 39 shows a lateral cross-section of an embodiment of an occluder where the balloon is stored inside the distal end of the cannula when the balloon is in its collapsed condition and expands out the end of the cannula.

In certain embodiments, the cannula is open at the distal end and the distal end has a lumen where the occluder, when contracted, is stored as shown in FIG. 39. This figure depicts an expanding balloon occluder 322. Upon expansion, the balloon advances out of the distal end of the cannula. As the balloon is inflated, more balloon material is available to expand, thus permitting occlusion of larger sized vessels once the balloon reaches its expanded condition 322'.

Figures 40, 41:
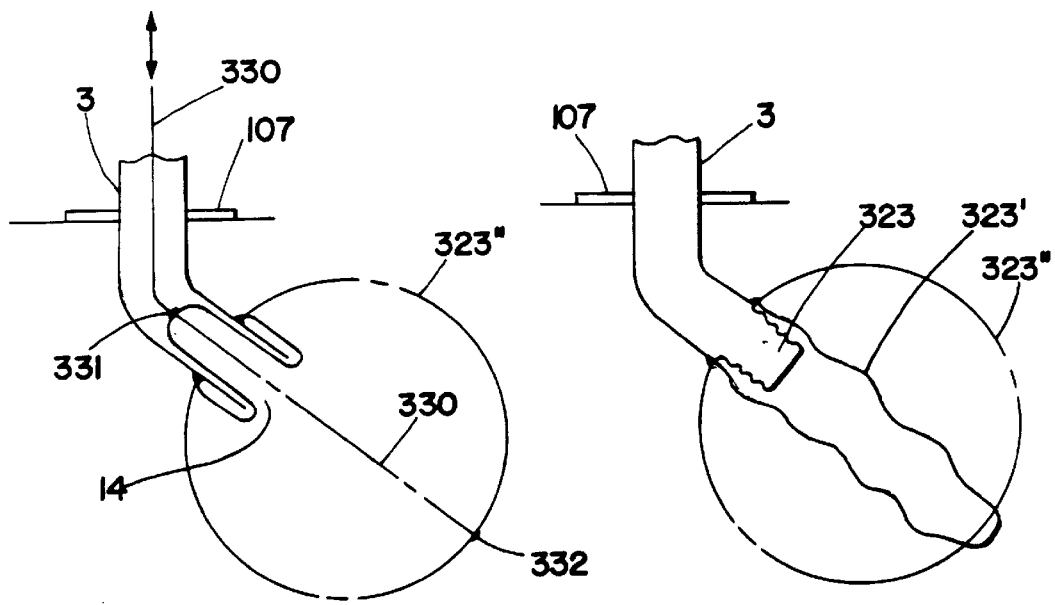
FIG. 40 shows a lateral cross-section of an embodiment of an occluder where the balloon includes an elastic line that is used to pull the collapsed balloon back into the end of the cannula.
FIG. 41 shows a lateral cross-section of an embodiment of an occluder where the balloon is shown in a collapsed, partially expanded and fully expanded condition.

FIG. 40 and FIG. 41 depict a cannula with an open distal end for storage of a contracted balloon occluder 323. The balloon can be retracted upon deflation into the distal end 14 of the cannula 3 by pulling on an elastic line 330 which passes through the lumen of the cannula. The elastic line 330 is coupled to the proximal end 331 of the balloon and the distal end 332 of the balloon, so that when the balloon is fully expanded 323", the elastic line is fully stretched. Upon deflation, the elastic line contracts and the distal end 331 of the balloon moves closer to the proximal end 332 of the balloon. The deflated balloon 332 may then be pulled into the distal end 14 of the cannula by pulling on the elastic line 330. FIG. 41 depicts the balloon in its initial contracted condition 323, a deflated condition 323' and a fully expanded condition 323", where the elastic line is not shown.

Figures 42, 43:
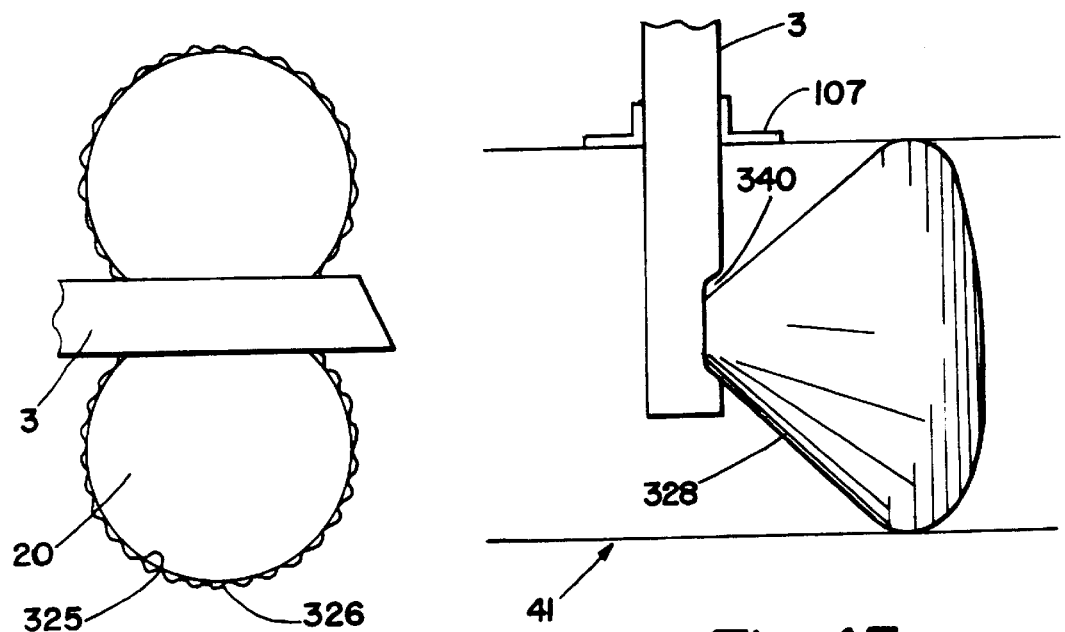
FIG. 42 depicts a lateral cross-section of an embodiment of an occluder where the balloon is an elastic material covered by a protective layer.
FIG. 43 depicts a lateral view of an embodiment of an occluder that is a funnel-shaped balloon expanding out the side of the distal end of the cannula.

In some applications it may be advantageous to cover the occluder with a protective layer. FIG. 42 shows a balloon occluder 20 disposed about the distal end of a cannula 3. The balloon 325 itself is made of an elastic material and its outer surface is covered by a protective material 326. In some embodiments, the protective layer itself has elastic capacity. In other embodiments, the protective layer is internal to the balloon so that the external surface of the protective layer is covered by the balloon material.

FIG. 43 depicts an embodiment where a funnel-shaped occluder 328 made of elastic material is deployed through a side opening 340 of the cannula 3. The funnel-shaped occluder 328 can occlude vessels of varying sizes due to its shape.

Figure 44:
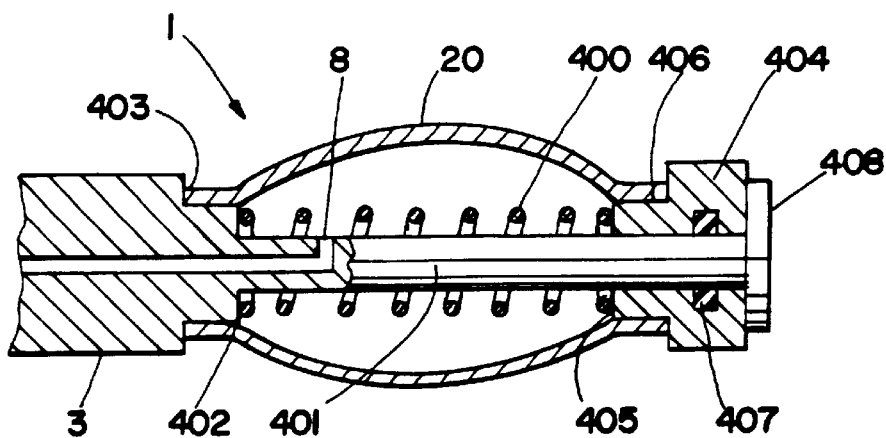
FIG. 44 depicts a lateral cross-section of an embodiment having an occluder aligner with a spring and an end sleeve shown with the occluder in a collapsed condition.
Figure 44A:
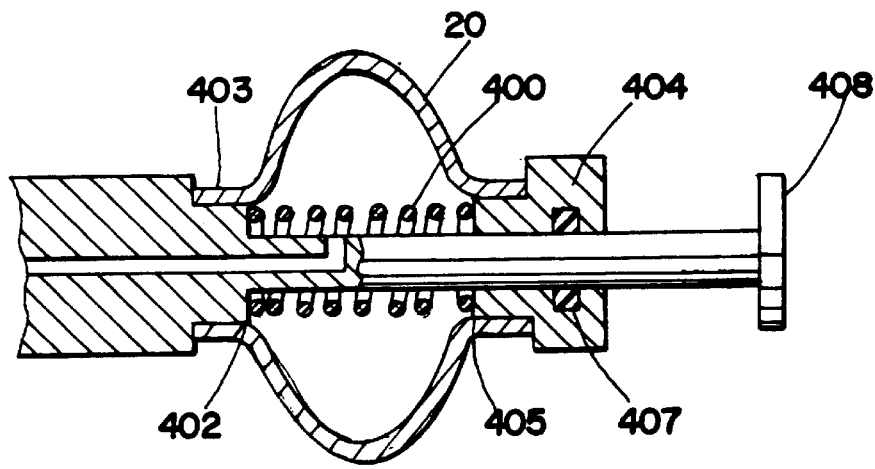
FIG. 44A depicts the embodiment of FIG. 44 with the occluder in an expanded condition.

Occluder aligners, which were described previously for manually aligning the distal end of the cannula, can also be used to provide position stability to expanding occluders. In some applications, an expanding occluder will "rock" out of position during expansion if the distal region of the cannula is not positioned along the center longitudinal axis of the aorta. Certain embodiments therefore include cannulas with occluder aligners of various designs to stabilize the position of the occluder and distal cannula during occluder inflation. One embodiment includes a longitudinally deformable region and an end sleeve which slides relative to the distal end of the cannula and is coupled to the longitudinally deformable region and to the occluder. During use, the occluder expands and the end sleeve moves proximally, thereby compressing the longitudinally deformable region. FIGS. 44 and 44A demonstrate this embodiment, where the longitudinally deformable region is a spring. FIG. 44 shows the distal region of the cardioplegia occluder 1 where the occluder 20 is in the collapsed condition. The spring 400 is coiled about the distal region 401 of the cannula inside the occluder chamber. The proximal end 402 of the spring is coupled to the region of the cannula inside the occluder chamber just distal to the proximal end of the occluder 403. The end sleeve 404 is disposed about the distal region of the cannula. The proximal end 405 of the end sleeve is coupled to the distal end of the spring 400. The end sleeve 400 is coupled to the distal end of the occluder in a region 406 of the end sleeve just distal to the proximal end of the sleeve. The end sleeve includes a seal 407 near the distal end of the sleeve adapted to surround the distal region of the cannula 3 so that this distal cannula region slideably inserts in the seal. The seal is adapted to prevent fluid in the occluder chamber from escaping from the occluder. In this embodiment, the occluder aligner includes an end stop 408 to prevent the end sleeve from sliding off the distal end of the cannula 3 during use. FIG. 44 also shows the location of the inflation port 8 inside the occluder chamber. FIG. 44A shows the embodiment of FIG. 44 where the occluder is in the expanded condition and the proximal end 405 of the end sleeve has moved along the distal region 401 of the cannula toward the proximal end of the occluder 403 and the spring 400 has compressed.

Figure 45:
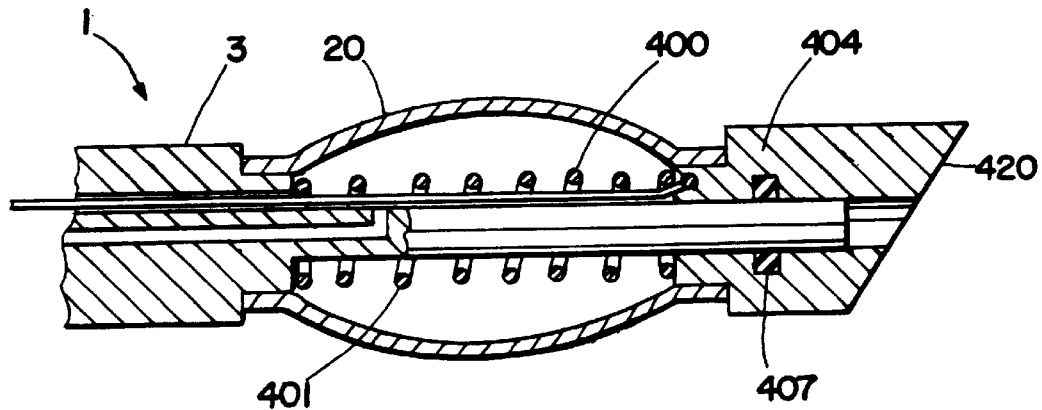
FIG. 45 shows the embodiment of FIG. 44 also having a cutting blade.

FIG. 45 depicts an embodiment of a cardioplegia occluder 1 that includes an occluder aligner where the distal end of the end sleeve 404 of the occluder aligner is a sharpened edge 420 that serves as a cutting blade. In use, the sharpened edge 420 creates the initial incision into the aorta and the cannula with the collapsed occluder is advanced into the lumen of the vessel. The occluder is expanded and the end sleeve 406 slides proximally along the distal region 401 of the cannula retracting the sharpened edge 420. In this embodiment, the longitudinally deformable region of the occluder aligner is a flexible tube.

Figure 46B:
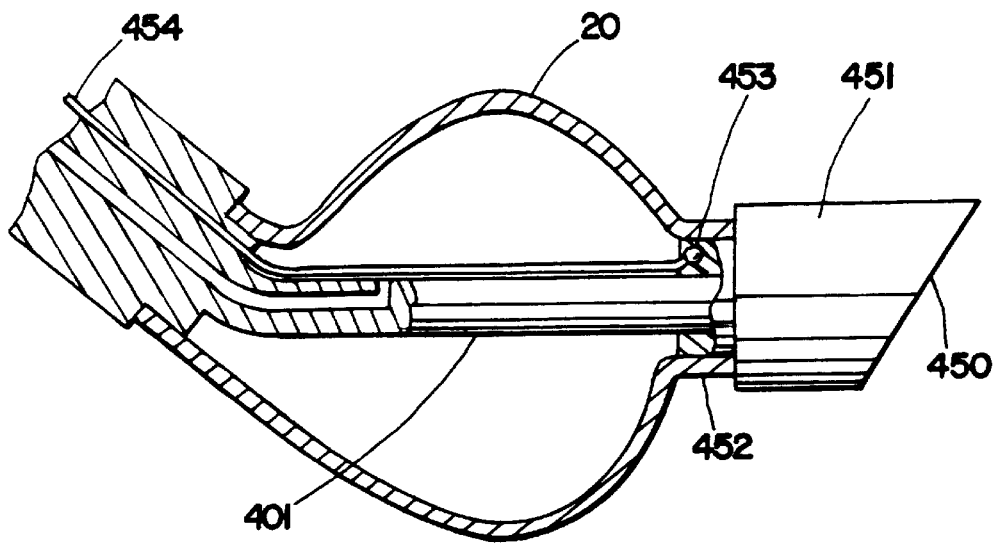
FIG. 46B is an enlarged view of the distal end of the embodiment of FIG. 46A.
Figure 46:
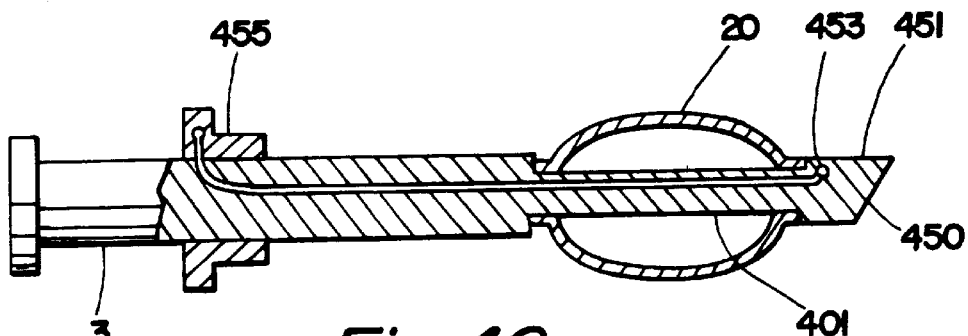
FIG. 46 shows a lateral cross-section an embodiment having a steering wire and a flexible tube occluder aligner where the occluder is in a collapsed condition.
Figure 46A:
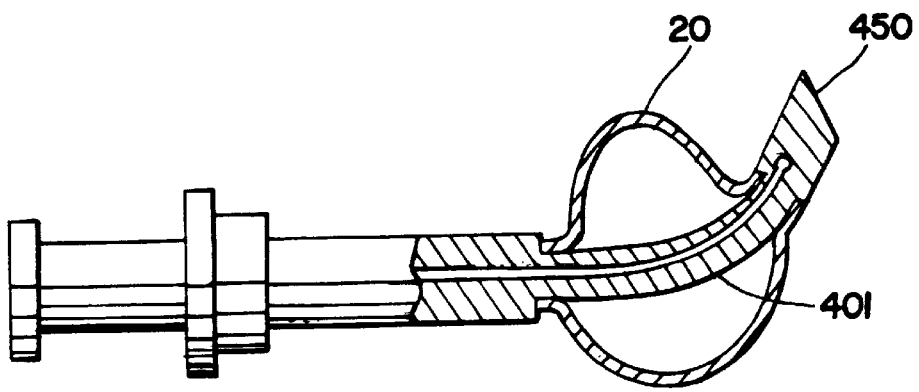
FIG. 46A shows the embodiment of FIG. 46 in an expanded condition where the steering wire has been manipulated to elevate the cannula tip.

An occluder aligner with a steering sleeve slideably mounted on the cannula and coupled to a steering wire is depicted in FIG. 46. In this embodiment, the steering sleeve 455 is disposed about the region of the cannula 3 proximal to the occluder 20, so that the cannula slideably inserts in the steering sleeve. The distal end 453 of the steering wire is coupled to the inner surface of the distal region of the cannula in the area where the occluder is coupled to the cannula. The steering wire 454 is carried by the cannula and is displaced from the longitudinal center of the cannula. In some embodiments, the steering wire passes through a hole or slot in the cannula which is distal to the region of the cannula which is inserted into the vessel. The proximal end 455 of the steering wire is coupled to the steering sleeve. In use, during occluder expansion, the steering sleeve is manipulated to move the distal end of the cannula. The steering sleeve can be moved along the cannula to elevate the distal end 450 as depicted in FIGS. 46A and 46B. Steerable occluder aligners can be designed so that the distal end of the cannula is positioned at the center point of the largest vessel in which the cardioplegia occluder is to be used. When used in smaller vessels, the tip will lie below the centerline and can be rotated up by pulling the steering sleeve distally.

As described previously, the cardioplegia occluder can be used in conjunction with other cardiopulmonary bypass equipment or other cardiac surgical equipment including blood cannulas, filter cannulas and diverters in various combinations as integrated systems or as separately insertable devices. In certain embodiments, a "one-stick" method is used, meaning that one incision is made into the aorta to insert the various pieces of equipment in either their integrated or separately insertable configurations. In other embodiments, "two-stick" or "three-stick" (two or three aortic incision) methods are used. In some embodiments, the occluder is mounted on the blood cannula instead of the cardioplegia cannula. TABLE 1, located at the end of the Detailed Description section, is provided to assist in describing the various combinations.

Figure 47:
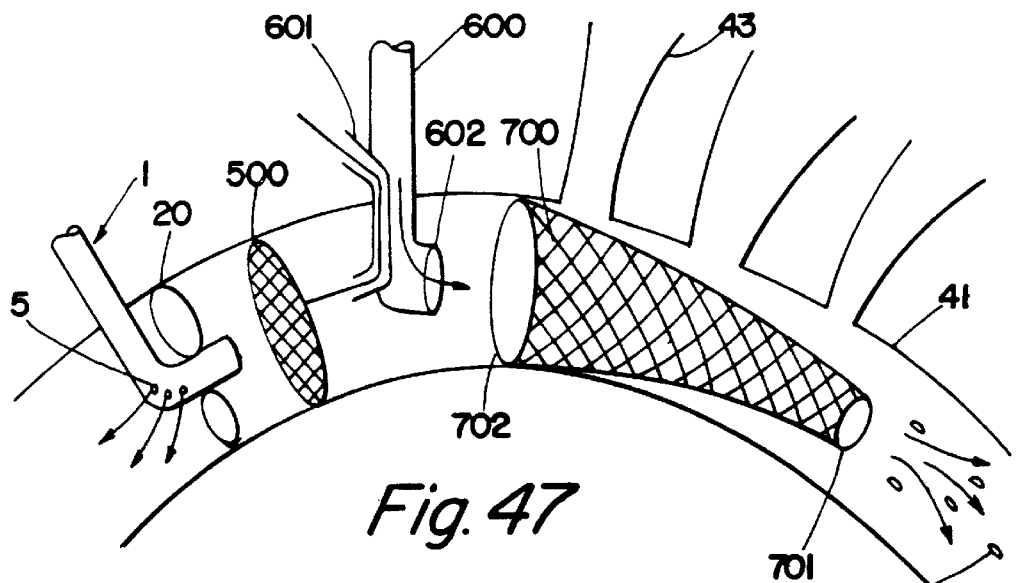
FIG. 47 depicts a cardioplegia occluder positioned inside the aorta upstream from a blood cannula having a side channel housing a separately insertable filter cannula, both upstream from a diverter.

FIG. 47 shows a two-stick embodiment with a blood cannula 600 (adapted to receive separately insertable filter 500 through a channel thereof) inserted through one incision and a separate cardioplegia occluder 1 inserted through a second incision. The filter is carried through side channel 601 of the blood cannula. Either a modular filter cannula as shown (see U.S. Pat. No. 5,846,260, incorporated herein by reference, for more details) or an integral filter cannula (see U.S. Pat. No. 5,769,816 and U.S. Ser. No. 08/553,137, filed Nov. 7, 1995, Ser. No. 08/580,223, filed Dec. 28, 1995, Ser. No. 08/584,759, filed Jan. 11, 1996, and Ser. No. 08/852,727, filed Apr. 16, 1997, all incorporated herein by reference, for more details) can be used. In this embodiment, a diverter 700 has been inserted in the region of the aorta 41 where the aorta intersects the brachiocephalic artery 43, the left subclavian artery and the left common carotid artery. In all cases described herein, whether one-, two- or three-stick and whether the various cannulas are integrated, separately insertable or certain cannulas are absent, the diverter may be (i) absent, (ii) inserted only for the purpose of conducting the cardiac surgery, then removed at the completion of the surgery, or (iii) permanently installed in the aorta. The embodiment of FIG. 47 allows the cardioplegia occluder 1 to occlude the aorta distal to the infusion ports 5 where cardioplegia solution is introduced to stop the heart. Downstream from the occluder 20, the filter 500 traps embolic debris and other unwanted material that is a byproduct of the surgical activity. Downstream from the filter, the blood cannula supplies blood from a heart lung machine to the aorta for circulation through the peripheral vasculature. The diverter 700, which is permeable to blood, further inhibits embolic material and other unwanted debris 800 from entering the cerebral vasculature by diverting it past the left common carotid artery and the brachiocephalic artery, which communicates with the right common carotid artery.

Figure 47A:
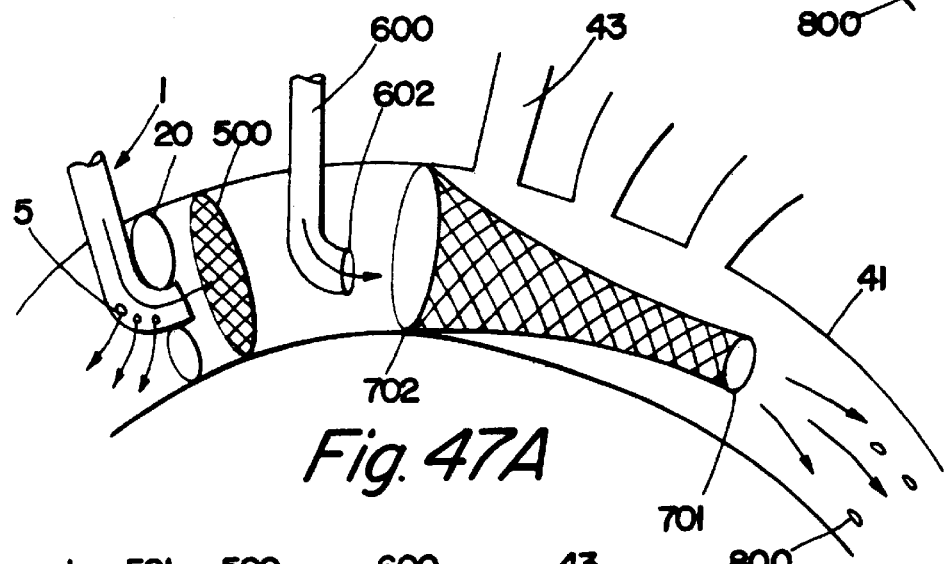
FIG. 47A depicts a cardioplegia occluder having a separately insertable filter cannula positioned inside the aorta upstream from a blood cannula which is upstream from a diverter.
Figure 49:
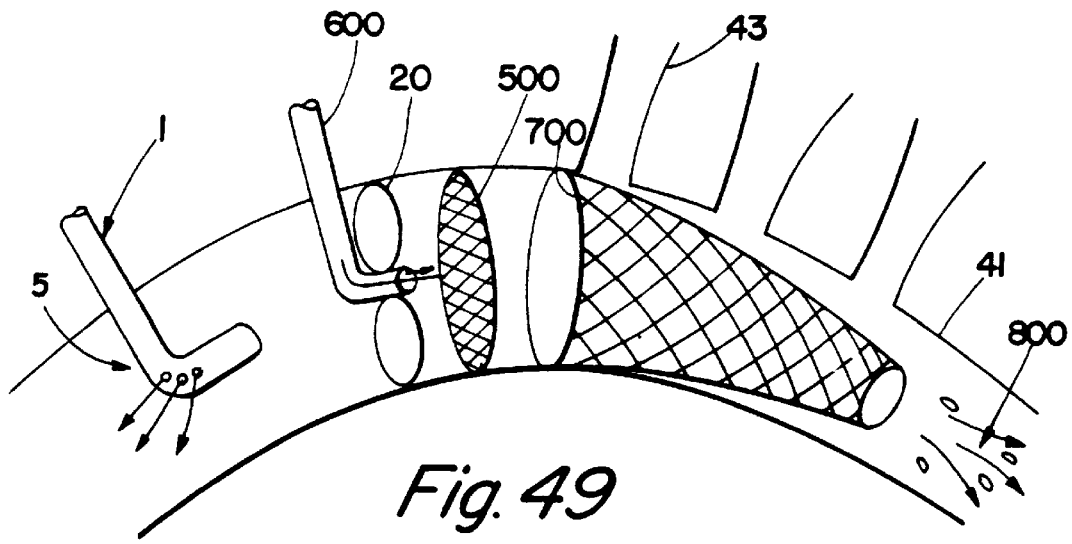
FIG. 49 depicts a cardioplegia cannula upstream from an occlusion blood cannula with a separately insertable filter, upstream from a diverter.

FIG. 47A shows an embodiment of a two-stick model where the cardioplegia occluder 1 is adapted to receive the filter 500 through a channel thereof, and the blood cannula 600 is inserted through a separate incision. A diverter is present, but as previously described, the diverter may be installed permanently, inserted only for the purpose of surgery or absent altogether in all one-stick, two-stick or three-stick methods. Other embodiments of the two-stick method include (i) an integrated cardioplegia occluder and blood cannula with a separate filter, either inserted through a filter cannula or separately inserted, (ii) a separately inserted cardioplegia occluder, a separately inserted blood cannula and no filter cannula, (iii) a blood cannula occluder with a filter inserted through a channel in the cannula as shown in FIG. 49, or mounted on the cannula and a cardioplegia cannula inserted through a separate incision, and (iv) a blood cannula occluder and a cardioplegia occluder inserted through a separate incision and no filter.

Figure 48:
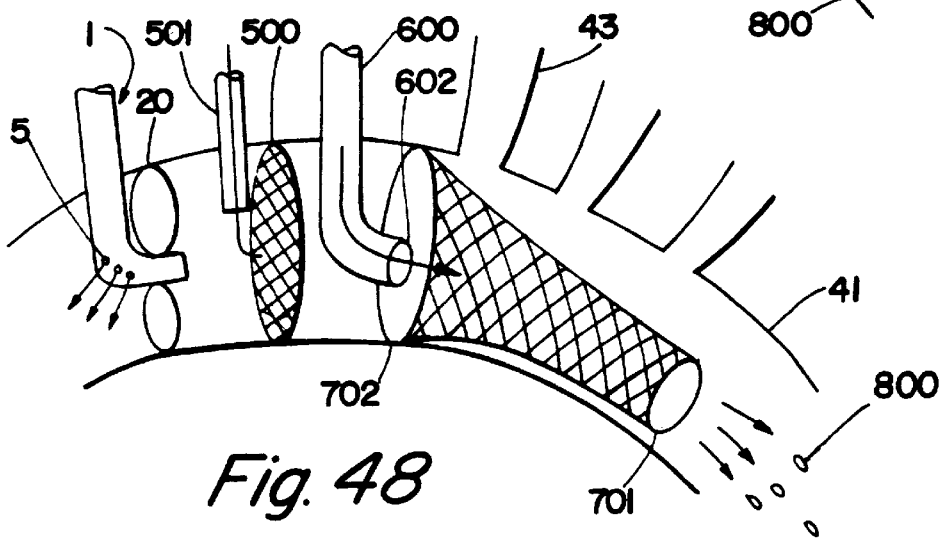
FIG. 48 depicts a cardioplegia occluder which is upstream from a filter cannula which is upstream from a blood cannula which is upstream from a diverter.
Figure 50:
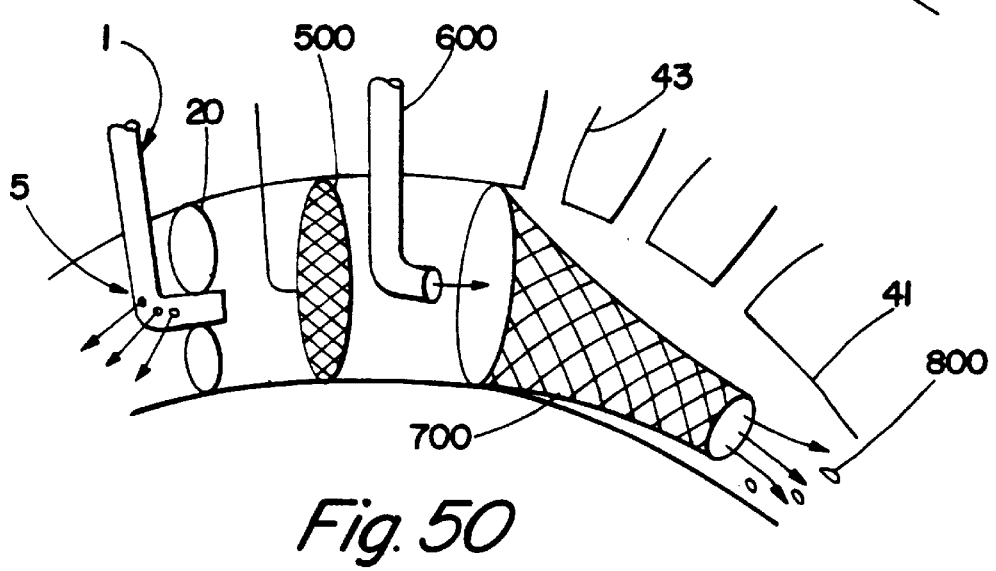
FIG. 50 depicts a cardioplegia occluder which is upstream from a separate stick filter which is upstream from a blood cannula which is upstream from a diverter.

FIG. 48 depicts a three-stick method with a separately inserted cardioplegia occluder 1, a separately inserted filter cannula 501 and a separately inserted blood cannula 600. In this embodiment, the diverter 702 is present, but any of the three diverter configurations could be utilized. In another embodiment, the filter is separately inserted without the use of a filter cannula, as shown in FIG. 50.

Figure 51:
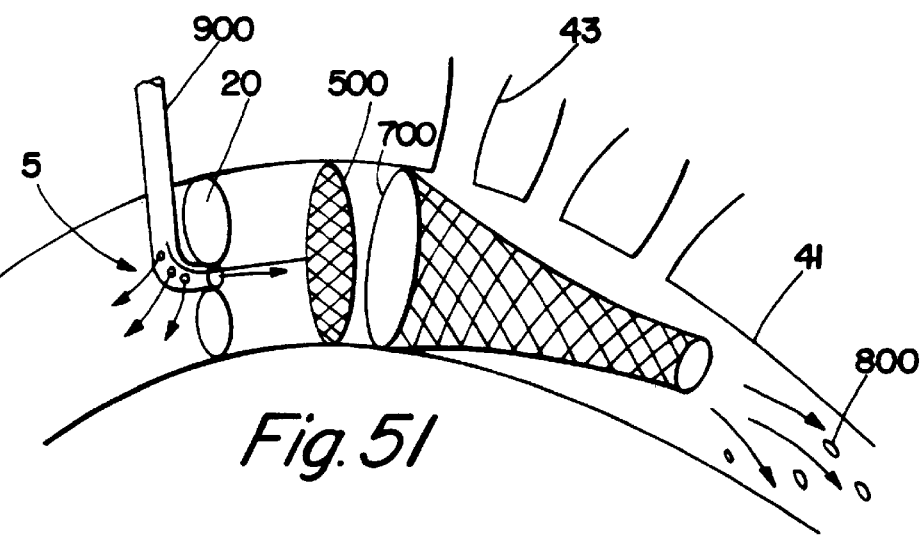
FIG. 51 depicts a cardioplegia occluder blood cannula which is upstream from a separately insertable filter which is upstream from a diverter.

In other embodiments, a one-stick method is used. In one embodiment, depicted in FIG. 51, the cardioplegia occluder and blood cannula are integrated 900, and the filter separately inserted through a channel in the cannula. In other embodiments, the filter may be mounted on the cannula or absent. Again, each combination has three possible diverter configurations.

In certain embodiments of the one-, two- and three-stick methods described above, the cardioplegia occluder may be replaced by a separate balloon cannula and a cardioplegia cannula. In such cases, the balloon cannula and the cardioplegia cannula can be separately inserted or can be integrated with one another or each integrated with the filter cannula or the blood cannula.

| | Cardioplegia occluder (CPO) | Filter (F) | Blood Cannula (BC) | Description |
|---|---|---|---|---|
| ONE-STICK* | | | | |
| (1a) | + | + | + | Integrated CPO/BC; filter separately inserted through cannula (FIG. 51) or mounted on cannula |
| (1b) | + | – | + | Integrated CPO/BC |
| TWO-STICK* | | | | |
| (2a) | + | + | + | Filter inserted through CPO (FIG. 47A) or mounted on CPO |
| 2b | + | + | + | Filter inserted through BC channel (FIG. 47) or mounted on BC |
| 2c | + | + | + | Integrated CPO/BC; filter through filter cannula or separately inserted |
| 2d | + | – | + | Separately inserted CPO and BC |
| 2e | CP | + | BCO | Occluder on BC; filter inserted through blood cannula occluder (BCO) (FIG. 49) or mounted on BCO, cardioplegia (CP) cannula separately inserted |
| 2f | CP | – | BCO | Occluder on BC, CP cannula separately inserted |

-continued

| Cardioplegia occluder (CPO) | Filter (F) | Blood Cannula (BC) | Description |
|---|---|---|---|
| THREE-STICK* | | | |
| (3a) | + | + | + | Filter separately inserted through filter cannula or without cannula |

*It is to be noted that each combination listed has three possible variants as to a diverter. The diverter may be (i) absent, (ii) inserted only for the purpose of conducting the cardiac surgery, then removed at the completion of the surgery, or (iii) permanently installed in the aorta.

While particular devices and methods have been described for using the cardioplegia occluder, once this description is known, it will be apparent to those of ordinary skill in the art that other embodiments and alternative steps are also possible without departing from the spirit and scope of the invention. Moreover, it will be apparent that certain features of each embodiment as well as features disclosed in each reference incorporated herein, can be used in combination with devices illustrated in other embodiments. Accordingly, the above description should be construed as illustrative, and not in a limiting sense, the scope of the invention being defined by the following claims.

We claim:

1. A method for administering cardioplegia, comprising the steps of:
   providing a substantially rigid cannula having proximal and distal ends, and a proximal and a distal region, a balloon occluder mounted on the distal region and communicating with an inflation lumen extending proximal from the occluder, a port on the cannula proximal the balloon, the port communicating with a first lumen which extends proximally from the port;
   making an incision in the aorta;
   inserting the distal end of the cannula and the occluder through the incision in the aorta;
   expanding the occluder to occlude the aorta downstream of the infusion port; and
   infusing cardioplegia solution through the port,
   wherein the occluder isolates the ascending aorta from peripheral circulation without substantial migration within the ascending aorta.

2. The method of claim 1, further comprising a second lumen which merges and communicates with the first lumen proximal the port.

3. The method of claim 1, wherein said cannula carries a cutting blade, and wherein the step of making an incision in the aorta is performed by the cutting blade.

4. The method of claim 1, wherein the occluder, when contracted, is adapted to conform to the outer surface of the cannula.

5. The method of claim 1, wherein the infusion port is proximal the occluder.

6. The method of claim 1, wherein the cannula further comprises an arterial return lumen which extends distally from the proximal end of the cannula and terminates and communicates with a second port.

7. The method of claim 6, wherein the second port is distal the occluder.

8. The method of claim 1, further comprising the step of placing the patient on cardiopulmonary bypass.

9. The method of claim 1, further comprising the steps of contracting the occluder and removing the cannula and the occluder from the aorta.

10. The method of claim 2, further comprising the step of aspirating fluid from the aorta by applying negative pressure to the second lumen.

11. The method of claim 1, further comprising the steps of performing a coronary artery bypass graft procedure.

12. The method of claim 1, wherein the distal region of the cannula is bent at an angle of approximately 90 degrees.

13. The method of claim 1, wherein the distal region of the cannula includes a curved region.

14. The method of claim 1, wherein the balloon covers a portion of the curved region.

15. The method of claim 1, wherein the cannula further comprises an inflation lumen which extends distally from the proximal end of the cannula and terminates and communicates with an interior of the balloon.

16. The method of claim 1, wherein the distal region of the cannula is tapered.

17. The method of claim 1, wherein the occluder expands to assume a generally spherical shape.

18. The method of claim 1, wherein said balloon occluder is made of an elastic material.

19. The method of claim 1, wherein the cannula further comprises a suture flange.

20. The method of claim 1, wherein the entire cannula is substantially rigid.

* * * * *